(12) United States Patent
Pinon et al.

(10) Patent No.: US 7,854,226 B2
(45) Date of Patent: Dec. 21, 2010

(54) POWDER INHALER

(75) Inventors: John Pinon, Tonnoy (FR); Sameer Shirgaonkar, London (GB); Christopher James Smith, Cambridge (GB); Simon Burge, Suffolk (GB); Max William Middleton, Cambridge (GB); David Ahern, Norfolk (GB); Matthew Neil Sarkar, Cambridge (GB); Ben Arlett, Cambridge (GB); Emma Lesley Lye, Cambridge (GB); Simon Smith, Hertford (GB)

(73) Assignee: Chiesi Farmaceutici S.p.A., Parma (IT)

( * ) Notice: Subject to any disclaimer, the term of this patent is extended or adjusted under 35 U.S.C. 154(b) by 979 days.

(21) Appl. No.: 11/407,520

(22) Filed: Apr. 20, 2006

(65) Prior Publication Data

US 2006/0185672 A1 Aug. 24, 2006

Related U.S. Application Data

(60) Division of application No. 11/045,631, filed on Jan. 28, 2005, now Pat. No. 7,107,988, which is a continuation of application No. PCT/EP03/008432, filed on Jul. 30, 2003.

(30) Foreign Application Priority Data

Jul. 31, 2002 (EP) .................................. 02016908

(51) Int. Cl.
*A61M 16/00* (2006.01)
*A61M 15/00* (2006.01)
*B05D 7/14* (2006.01)
*B65D 83/06* (2006.01)

(52) U.S. Cl. .............................. 128/203.15; 128/203.12

(58) Field of Classification Search ............ 128/203.12, 128/203.15, 200.14, 200.18, 200.22, 203.19, 128/203.21, 203.22, 203.24, 203.28
See application file for complete search history.

(56) References Cited

U.S. PATENT DOCUMENTS 2,587,215 A 2/1952 Priestly
5,020,527 A 6/1991 Dessertine (Continued)

FOREIGN PATENT DOCUMENTS

CA 2093809 8/1992

(Continued)

*Primary Examiner*—Justine R Yu
*Assistant Examiner*—Colin Stuart
(74) *Attorney, Agent, or Firm*—Holme Roberts & Owen LLP

(57) ABSTRACT

A powder inhaler includes a container for storing powdered medicament. A metering member has a dosing recess and is moveable between a filling position in which the dosing recess is in alignment with an opening of the container, and an inhalation position in which it is in alignment with an inhalation channel. A mouthpiece is in communication with the inhalation channel for enabling inhalation of the dose of powdered medicament when in the inhalation position. A protective member provided between the metering member and the inhalation channel is moveable between a closed position in which the protective member covers the dosing recess, thereby preventing powdered medicament contained in the dosing recess from entering the inhalation channel, and an open position in which the protective member does not cover the dosing recess, thereby exposing the dosing recess to the inhalation channel for enabling inhalation of the dose of the powdered medicament.

17 Claims, 16 Drawing Sheets

U.S. PATENT DOCUMENTS

| | | | |
|---|---|---|---|
| 5,113,855 A | 5/1992 | Newhouse | |
| 5,161,524 A | 11/1992 | Evans | |
| 5,447,151 A | 9/1995 | Bruna | |
| 5,476,093 A | 12/1995 | Lankinen | |
| 5,524,613 A | 6/1996 | Haber et al. | |
| 5,875,774 A * | 3/1999 | Clementi et al. | 128/200.18 |
| 6,073,629 A | 6/2000 | Hardy et al. | |
| 6,123,070 A * | 9/2000 | Bruna et al. | 128/203.15 |
| 6,182,655 B1 | 2/2001 | Keller et al. | |
| 6,418,926 B1 | 7/2002 | Chawla | |
| 6,505,622 B2 * | 1/2003 | Py | 128/203.18 |
| 6,718,972 B2 | 4/2004 | O'Leary | |
| 2002/0078949 A1 | 6/2002 | O'Leary | |
| 2002/0088463 A1* | 7/2002 | Keane et al. | 128/203.21 |
| 2003/0015195 A1* | 1/2003 | Haaije de Boer et al. | 128/203.15 |

FOREIGN PATENT DOCUMENTS

| | | |
|---|---|---|
| EP | 0 079 478 | 10/1982 |
| EP | 0 166 294 | 6/1985 |
| EP | 0 237 507 | 9/1987 |
| EP | 0 477 222 | 6/1990 |
| EP | 0 546 996 | 12/1992 |
| EP | 0 758 911 | 5/1995 |
| EP | 0 865 302 | 2/2001 |
| FI | 8 710 000 | 3/1987 |
| FR | 2 352 556 | 12/1977 |
| FR | 2701653 A1 | 8/1994 |
| FR | 2667509 | 9/1995 |
| GB | 2 165 159 | 4/1986 |
| GB | 2353222 A | 2/2001 |
| HU | 213774 | 11/1995 |
| HU | 220 182 | 9/2000 |
| HU | 223 431 | 6/2003 |
| WO | WO9015635 A1 | 12/1990 |
| WO | WO 92/00771 | 1/1992 |
| WO | WO 92/09322 | 6/1992 |
| WO | WO 92/10229 | 6/1992 |
| WO | WO 93/03782 | 3/1993 |
| WO | WO 94/04210 | 3/1994 |
| WO | WO9428957 A1 | 12/1994 |
| WO | WO9532752 A1 | 12/1995 |
| WO | WO 9826828 A2 * | 6/1998 |
| WO | WO 01/00262 A1 | 1/2001 |
| WO | WO 02/07805 A2 | 1/2002 |
| WO | WO 2004/012802 | 2/2004 |

\* cited by examiner

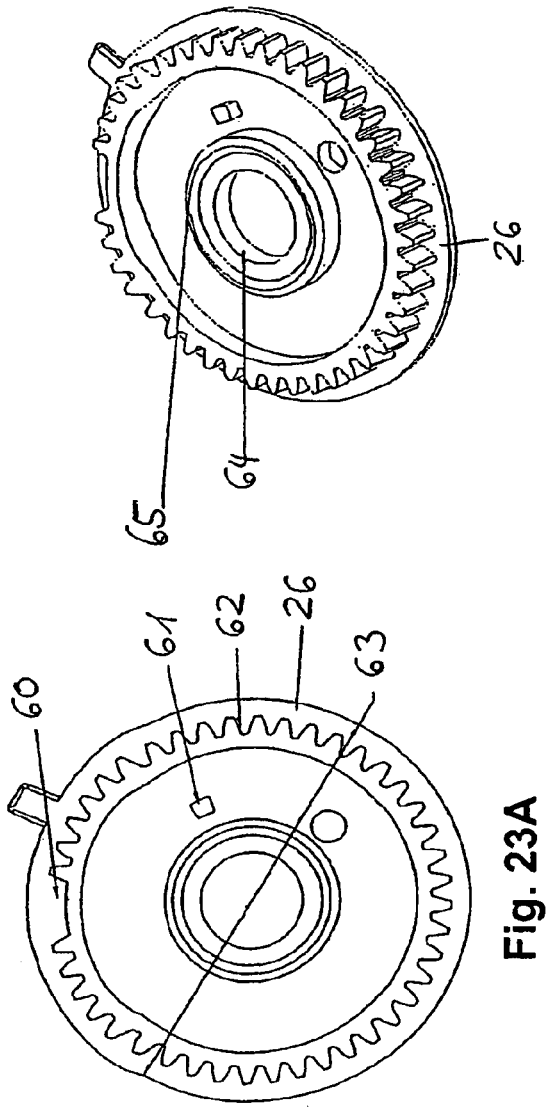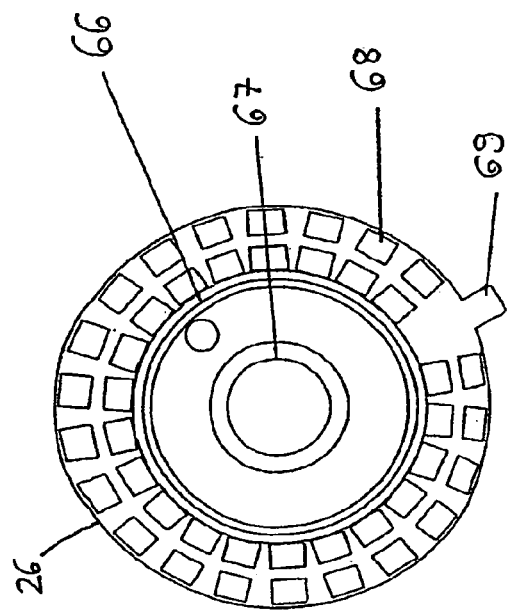
Fig. 23B
Fig. 23C
Fig. 23A

POWDER INHALER

CROSS-REFERENCE TO RELATED APPLICATIONS

This application is a divisional of application Ser. No. 11/045,631, filed on Jan. 28, 2005 now U.S. Pat. No. 7,107,988, which is a continuation of the Patent Cooperation Treaty application PCT/EP2003/008432, having an international filing date of Jul. 30, 2003, which claims priority to EP 02016908.2, having a filing date of Jul. 31, 2002, all of which are incorporated herein in their entirety and to which priority is claimed.

BACKGROUND OF THE INVENTION

1. The Field of the Invention

The present invention relates to a powder inhaler, i.e. a device for dispensing a powdered medicament preparation by inhalation. The device is in particular a portable multiple-dose device without propellant gas, equipped with a metering member which dispenses doses from a medicament container. Moreover, the device is based on centripetal force for achieving a more effective pulverization of the powdered inhalation medicament in such a manner that the penetration of the medicament into the lungs of a patient is improved and the adhesion to the upper respiratory passages is reduced for alleviating possible side effects caused thereby.

2. The Relevant Technology

The administering of a powdered medicament preparation by inhalation from an inhaler is commonly known. Multiple-dose type powder inhalers comprising a powder container and a metering member which measures and dispenses a unit dose are also known, for example from patent publications GB 2165159, EP 0 079 478, and EP 0 166 294. In these devices, a series of dosing recesses are notched into the surface of a cylindrical metering member, and the member is disposed in a chamber of precisely the same shape. When the metering member is rotated, the dosing recesses in turn will move first to a position in alignment with the powder container for being filled and thereafter to a position in alignment with an inhalation channel, whereupon a unit dose will fall by gravity from the dosing recess into the inhalation channel. Thereafter the dose of medication is inhaled from the inhalation channel. These devices have the drawback that they make overdosing of the medicament possible by allowing the dispensing of a plurality of doses in succession into the inhalation channel, whereby a multiple dose may be drawn by one inhalation.

Inhalation devices having a metering plate movable between a filling and a dispensing position are described e.g. in patent publications WO 92/10229, U.S. Pat. Nos. 5,113,855, and 2,587,215, EP 0 546 996, WO 94/04210 and U.S. Pat. No. 5,161,524. A further example of related devices is given in WO 93/03782. However, these devices also suffer from a drawback that they make overdosing possible by allowing the dispensing of a plurality of doses into the inhalation channel.

Attempts have been made to solve this problem by using inhalers or dispensing systems in which the dosing recess will not be emptied into the inhalation channel by gravity but, instead, the dose of medication is inhaled directly from the dosing recess, such recesses having been notched into the surface of a metering member. The metering member may have the shape of a cylinder, a cone or a truncated cone, as disclosed in patent publications WO 92/00771 and WO 92/09322. Furthermore, in these devices, the metering member having the shape of a cylinder, a cone or a truncated cone is disposed in a chamber having precisely the same shape. When the metering member is rotated, the dosing recesses will move first to a position in alignment with the medicament container for filling, and then to the inhalation channel which is shaped so that the respective dosing recess will be emptied under the effect of the air flow being inhaled, and thereafter, having rotated through a full 360°, back to a position in alignment with the medicament container. The lower surface of the chamber wall may also have an emptying aperture from which any powdered medicament possibly left in the dosing recess will fall out during the rotation.

In the rotating dispensing devices described above, the distance from the filling position to the inhalation position is less than 90° of a circle arc. Since the metering member is, for purposes of metering precision, disposed within a chamber of the same shape, and since it has to be rotated through 360°, of which at least 270° are useless for the actual function of the inhaler, in these devices particles will inevitably fall onto the slide surface between the metering member and the chamber. Thereby the rotation of the highly sensitive metering member will be disturbed and may even be completely obstructed. The metering member jamming inside the chamber will hinder the functioning of the whole device. Vigorous shaking or tapping will only increase the jamming as more powder flows into the gap between the chamber and the metering member.

An improvement of the powder inhalers of the related art is suggested in EP 0 758 911. The described powder inhaler comprises a powder container, an air channel through which air is drawn via a mouthpiece, and a metering member equipped with a dosing recess, the metering member being movable in its longitudinal direction between a first position, in which the dosing recess is filled with powder coming from the container, and a second position, in which the filled dosing recess is brought into the air channel, the powder being maintained in the recess by the support of the recess bottom, and the air channel being directed to introduce the air flow into the bottom of the dosing recess during inhalation whereby the powder is released directly from the dosing recess. According to the powder inhaler of this related reference, the metering member is a metering strip which is disposed on a flat surface and moves along the flat surface. When moving between the filling and the inhalation positions, the metering strip travels over an aperture for remnants, at which time any powder possibly remaining between the metering strip and the flat surface will fall out through the aperture. This powder inhaler is still not completely satisfying for the following reasons, e.g. the inhaled air flow is directed longitudinally relative to the metering strip. In this condition both the deaggregation of the powder and the removal of the powdered medicament from the metering strip by the inhaled air flow is not efficient. Moreover, any powder possibly left after the inhalation will remain in the air channel until the metering strip again moves along the flat surface into the air channel during a subsequent inhalation process. This remaining powder could be accidentally inhaled by the patient. Furthermore, the powder remaining inside the air channel may deteriorate due to the friction between the surfaces.

As mentioned above, a further problem with respect to powder inhalers is that a sufficient deaggregation of the powder and the removal of the powdered medicament or drug from the metering member by the inhaled air flow is not satisfactory in the powder inhalers of the related art.

It is generally known that the size of medicament particles should be 1-5 microns, preferably 2-3 microns, for the best possible penetration into their destination, i.e. deep into the lungs. The most common metering device is a so-called inhalation aerosol which is quite readily capable of reaching the optimal particle size. In addition to inhalation aerosols, an increasing number of powder inhalers are presently in use as these offer certain benefits, e.g. there is no need for ozone-destroying propellants. However, a drawback of powder inhalers is that a powdered medicament issuing from the powder inhaler has a too large particle size. Thus, most of the medicine dosage coming out of inhalers is retained in upper respiratory passages which, with certain medicines, can cause serious side effects. The medicine dosages required for different inhalation medicaments vary considerably, the smallest being approximately 0.01 mg and the largest 20 mg. When small amounts of medicine are metered in powdered form, it is generally necessary to use some adjuvant or carrier, so that the sufficiently precise measuring of a dosage would be possible with the present technology. No matter if the dosage comprises just medicine or has a carrier admixed therein, the medicine dosage substantially comprises inter-adhered particles and most of these agglomerates are too large to penetrate into the lungs. As the agglomerates are released in a powder inhaler into an air flow directed into the lungs of a patient, some dispersal of these particle deposits can occur, the dispersal resulting from the formulation of a powdered medicament and the construction of an inhaler. It is known that constructions creating a strong turbulence are capable of more effective pulverization.

In practice, however, no prior known powder inhalator structure and/or medicine formulation has produced results that would be equal to those achieved by an ordinary inhalation aerosol. It has been suggested as a partial solution that inhalation should be effected with as much force as possible, whereby the turbulence and pulverization of particles would accordingly be most effective. However, a quick inhalation is difficult for a person suffering e.g. from serious asthma and, on the other hand, a quick inhalation increases the residue in upper respiratory tracts. According to studies, pulverization of agglomerates is indeed intensified but the overall benefit is marginal. Excellent Pulmonary penetration in relation to the adherence of medicament to the upper respiratory tracts has been achieved by slow inhalation, corresponding to a flow rate of approximately 30 l/min or 0.5 l/sec.

Finnish patent application No. 871000 discloses a powder inhalator which has been designed in an effort to produce a clearly defined turbulence for pulverizing agglomerations of medicine. The centrally directed deflectors inside the device or the helical chute are explained to set the air flow in a spinning motion, whereby the medicine particles entrapped in the air abrade as a result of centrifugal force against the walls of the structure as well as collide with each other with resulting pulverization. The device described in the cited application has been marketed under the trade name Turbohaler® (Draco, Sweden), and the pulverizing structure therein is, as described above, a helical chute or groove. Laboratory tests indicated that this device had a relatively good pulverization of agglomerates of medicine which, however, could still be improved and intensified. In view of the pulverization of agglomerates or accumulations of medicine, there are a few defects in this device. The helical groove has in the centre thereof an open space having less air resistance than inside the groove. Accordingly, the flow rate of air and centrifugal force on the circumference of the groove are less than theoretically possible. Since the particles advance in the groove under a force caused by air resistance and centrifugal force tends to push the particles perpendicularly to the circumferential tangent, the actual force applied to the particles is a resultant of these forces and is applied diagonally relative to the circumferential tangent. Thus, the centrifugal force resulting from the spinning motion cannot be utilized in full extent for the pulverization of accumulations. In all deflector structures according to the cited application, the particles escape from the device within a few thousandths of a second when using conventional inhalation rates of 30-90 l/min, and that is a very short time for an effective pulverization. The residence time can be prolonged, e.g. by increasing the number of helices in groove portions or the number of separate deflector structures or the length of zigzagging air flow channels, but this would complicate manufacturing and cleaning and medicine residues in the actual device would increase. After all, cleaning of the structures disclosed in the cited application is difficult.

EP 0 407 028 shows in its FIGS. 5 to 7 a vortex chamber into which an inlet tangentially directs air with a pulverized medicament. The dispersion air/medicament leaves the chamber axially at an outlet. Nothing is said about the diameter of the chamber.

FR-A-2352556 shows a cylindrical vortex chamber closed at one end, operated by the action of inhalation and having one tangential air-medicament inlet duct, an additional tangential air inlet duct and an axial outlet duct near the same end of the chamber as the inlet duct. The outlet is formed by a tube-like connection extending beyond the zone of the inlet duct and impeding the air flow. Nothing is said again about the diameter of the cylindrical chamber.

Moreover, in the device described in EP 0 477 222 a powdered medicament intended for inhalation is pulverized on the basis of a sufficiently powerful centrifugal force prior to or during inhalation. The centrifugal force is produced by the action of inhalation. A powdered medicament is entrapped in a gas flow and forced in a substantially circular or rotationally symmetrical space to such a powerful rotating motion that an effective splitting of accumulations of medicine is obtained. This is affected in a rotationally symmetrical chamber whose largest internal diameter can be 20 mm. The optimum diameter of the vortex chamber operating by the action of inhalation is 10-20 mm. If the diameter is increased, the pulverization effect deteriorates in a manner that, with a diameter of more than 30 mm, the pulverization effect is no longer significant.

From EP 0 865 302, a further powder inhaler is known which comprises a medicament container for storing a dry powdered medicament, a mouthpiece being covered by a removable protective cap, and a movable dosing slide having a dosing cavity to be placed underneath a funnel outlet of the medicament container for filling. With opening of the protective cap, the movable dosing slide with the filled dosing cavity is pushed into a shutter, and the dosing cavity is closed thereby. Upon a sufficient suction force generated by an inhalation process, a valve shield pushes away the shutter, and the dosing cavity is released in order to enable inhalation of the medicament powder. Furthermore, means are provided for enabling the return of the dosing slide only after a correctly completed inhalation process. A recording unit records the number of correctly performed inhalations and blocks the powder inhaler after a predetermined number of inhalations. Between the inlet and the outlet of the mouth-piece a labyrinthine atomiser path for powder deagglomeration is provided.

BRIEF SUMMARY OF THE INVENTION

The technical problem underlying the present invention is to eliminate the above drawbacks of hitherto known powder inhalers and to provide a powder inhaler with an improved functionality. In particular, it is an aspect underlying the present invention to provide a powder inhaler with an improved dosing ability, whereby unintended dosing can be avoided, and to provide a powder inhaler with an optimal pulverization of agglomerates of a medicament to be inhaled, respectively.

This technical problem can be solved by a powder inhaler having the following features a container for storing a powdered medicament, a metering member having a dosing recess, the metering member being moveable between a filling position, in which the dosing recess is in alignment with an opening of the container so as to be filled with a dose of the powdered medicament, and an inhalation position, in which the dosing recess is in alignment with an inhalation channel, and a mouthpiece being in communication with the inhalation channel for enabling inhalation of the dose of the powdered medicament contained in the dosing recess of the metering member when the metering member is in the inhalation position. A protective member can be provided between the metering member and the inhalation channel, the protective member being moveable between a closed position, in which the protective member at least covers the dosing recess of the metering member when the metering member is in the inhalation position, thereby preventing the powdered medicament contained in the dosing recess from entering into the inhalation channel and an open position, in which the protective member does not cover the dosing recess, thereby exposing the dosing recess to the inhalation channel so as to enable inhalation of the dose of the powdered medicament contained in the dosing recess.

Furthermore, a deagglomerator arrangement for deagglomerating a powdered medicament can include a vortex chamber having an opening for the supply of the powdered medicament, at least two air inlets for directing air tangentially into the vortex chamber, and an outlet for outputting air with the deagglomerated powdered medicament. The outlet can be spaced from the air inlets in an axial direction of the deagglomerator arrangement. An outer wall of each air inlet can be connected to the other air inlet by an arched wall portion of the vortex chamber, each arched wall portion being positioned non-concentric to a horizontal circle defining a diameter of the vortex chamber.

In addition, the powder inhaler can include an inhalation channel having a deagglomerator arrangement as described above, which may be incorporated into such a powder inhaler without, however, being limited to this preferred use. These and other aspects and features of the present invention will become more fully apparent from the following description and appended claims, or may be learned by the practice of the invention as set forth hereinafter.

According to the present invention, a powder inhaler is provided comprising a container or a powder reservoir for storing a powdered medicament, a metering member having a dosing recess to be filled with one dose of the powdered medicament, a mouthpiece being in communication with an inhalation channel, and a protective member being provided between the metering member and the inhalation channel. The metering member is moveable between a filling position, in which the dosing recess is in alignment with an opening of the container so as to be filled with one dose of the powdered medicament, and an inhalation position, in which the dosing recess is in alignment with the inhalation channel. The protective member is moveable between a closed position, in which it at least covers the dosing recess when the metering member is in the inhalation position, thereby preventing the powdered medicament contained in the dosing recess from entering into the inhalation channel, and an open position, in which the protective member does not cover the dosing recess, thereby exposing the dosing recess to the inhalation channel so as to enable inhalation of the dose of the powdered medicament contained in the dosing recess.

The protective member, which is preferably a thin plate sliding on the metering member between its closed position and its open position, prevents the drug or powdered medicament contained in the dosing recess from falling out of the dosing recess, thereby preventing an unintentional loss of the powdered medicament contained in the dosing recess. Although a manual movement of the protective member between its closed position and its open position is conceivable, the protective member is preferably automatically withdrawn and moved from its closed position into its open position upon an inhalation process, thereby enabling the powdered medicament contained in the dosing recess to be released into the inhalation channel. Thus, the powder inhaler can be used in a variety of orientations, even upside down when the user or patient is lying in a bed, for example. This is a distinctive advantage over related art products where the dose can be lost by a poor orientation of the device.

In order to automatically withdraw the protective member from its closed position and move it into its open position upon an inhalation process, an inhalation actuated mechanism may be provided being coupled to the protective member such that, if the protective member is in its closed position, the inhalation actuated mechanism moves the protective member into its open position if the inhalation suction force of the respective user exceeds a predetermined value. Preferably, the inhalation or breath actuated mechanism is constructed such that it automatically returns the protective member into its closed position after the respective inhalation process has properly been completed.

The powder inhaler of the present invention may comprise a casing and an integral cover, the integral cover being rotatably or pivotably coupled to the casing so as to enable opening and closing of the integral cover. The casing may comprise a window or an opening for displaying the number of doses taken or the number of doses left in the container, this number being counted by a dose counting unit. If the cover is closed it covers the mouthpiece being located at the upper side of the casing. The casing may also comprise an opening for a mark, for example in the form of a flap, which shows if a dose is ready for inhalation or not. In particular, this flap may disappear upon completion of an inhalation process, thereby showing that the respective dose has been taken by the user.

The container storing the powdered medicament is preferably divided up into a medicament chamber storing the powdered medicament and a desiccant chamber for storing a desiccant provided for drying out the powdered medicament contained in the medicament chamber, the desiccant chamber being separated from the medicament chamber by a separate permeable membrane. The permeability of the membrane is different from, in particular greater than that between either the desiccant or the medicament and the outside world. This can be achieved, for example, by making the membrane from a different material and/or a thinner material than the main body of the container. Both the medicament chamber and the desiccant chamber may be sealed by foils. The bottom of the medicament chamber may have a dosing opening so that the powdered medicament contained therein can be filled into the dosing recess of the metering member supported by gravity, if the metering member is in its filling position. The filling process is furthermore supported by an appropriate shape of the medicament chamber which should have a cross-section diameter gradually decreasing from its top to its bottom, thereby forming a funnel for the powdered medicament.

The metering member is preferably a slide or a shuttle which is provided within the casing slidingly moveable in the horizontal direction between the filling position and the inhalation position. In the filling position the dosing recess faces the dosing opening of the container, and in the inhalation position the dosing recess faces an inhalation opening of the inhalation channel being in communication with the mouthpiece. The slide is preferably coupled to the cover such that opening of the cover causes the slide to move from the filling position forward to the inhalation position, and closing of the cover causes the slide to move from the inhalation position backward to the filling position. Projections, for example in the form of bolts, may be formed at both longitudinal sides of the slide, these projections engaging with profiled cam tracks being formed at the respective sides of the cover. This allows the fundamental operating sequence of the powder inhaler to include opening the cover, inhaling the dose, and closing the cover. It is the simplest possible operating sequence to reduce training time on the one hand and maximize patient compliance on the other hand.

The coupling between the cover and the metering member is preferably such that opening of the cover by a predetermined first angle from its closed position, preferably by an angle up to about 30°, does not actuate the metering member at all. Within this range of movement of the cover is slack where no mechanism is driven. Furthermore, the coupling between the cover and the metering member is preferably such that the metering member is moved in its inhalation position already a predetermined second angle prior to the cover being fully open. For example, the metering member may be placed in its inhalation position already when the cover has been opened by about 90° from its closed position. Between an opening angle of about 90°-135°, for example, there is free play again. This ensures that, should the user attempt a discrete operation of the device, the drug or the powdered medicament is ready already prior to the mouthpiece becoming exposed to the user.

The dosing recess may be designed to maximize the accuracy of gravitationally filling the dosing recess with the powdered medicament and also to maximize the ease of airborne entrainment of the formulation upon inhalation. Therefore, the dosing recess may be a dosing cup which is circular in profile and has an elliptical cross-section, the diameter being preferably three times the depth thereof. This enables the inhalation airflow to scour the dosing cup effectively. The circular profile and the ratio of depth to top area also combines the lowest variability of filling (primarily associated with deep, narrow receptacles) and scraping upon leaving the container (primarily associated with shallow, wide receptacles).

The flat surface of the metering member may be provided with a slot so that, upon a backward movement of the metering member from its inhalation position to its filling position, any powdered medicament possibly left on the flat surface of the metering member outside the dosing recess is wasted through the slot and can fall into a waste bin being provided underneath the metering member so as to catch this resilient powdered medicament. In this way, even when the dose was not completely inhaled by the user, there is no remaining medicament in the inhalation channel.

The inhalation actuated mechanism may comprise an inhalation actuated means/member, a resilient means/member, and a coupling means/member. The resilient member, which is preferably a spring, has a first end which holds the inhalation actuated member in a first position. In this condition, the aforesaid mark, which is preferably a flag, is visible through the respective opening of the casing, thereby indicating that a dose has not been taken and is ready for inhalation, respectively. The inhalation actuated member is preferably a flap.

Upon forward movement of the metering member from its filling position to its inhalation position, the resilient member is charged up or tensioned, thereby releasing the inhalation actuated member. The inhalation actuated member is arranged and constructed such that, in this condition, only a predetermined inhalation suction force of a user, however not blowing, can move the inhalation actuated member out from its first position into a second position. For example, in this case, the inhalation actuated member may pivot or rotate from its first position into its second position. Thereby, the mark of the inhalation actuated member disappears and is no longer visible through the respective opening in the casing, indicating to the user that a dose has been taken and, thus, currently no dose is ready for inhalation. The inhalation actuated member, the resilient member, and the coupling member are also arranged and constructed such that the inhalation actuated member holds the coupling member, which is preferably in the form of a yoke, in a first position. The coupling member is coupled to the protective member, and preferably also to the metering member.

When the inhalation actuated member is moved from its first position to its second position by a sufficient inhalation force effected by a user, the coupling member is released and, by the discharging effect of the resilient member, automatically moved into its second position in which the coupling member automatically moves the protective member from its closed position into its open position, thereby releasing the dose contained in the dosing recess. For example, the coupling member may have an arm which is released upon movement of the inhalation actuated member from its first position into its second position, and the coupling member may also comprise a prolonged projection which, on the one hand, engages an opening of the protective member and, on the other hand, is slidingly moveable within a slide formed in the metering member.

When the cover of the powder inhaler is closed again, the metering member is returned to its filling position, and the aforesaid dose counting unit is actuated and incremented. In particular, this is effected as follows:

The coupling member may comprise a further prolongation, preferably in the form of a cantilever, which, when the metering member causes the coupling member to move back from its second position to its first position, actuates the dose counting unit. In this regard, the dose counting unit may comprise a wheel arrangement having a plurality of wheels being numbered on one side facing the opening of the casing of the powder inhaler and being coupled to each other by a gear arrangement. In particular, the wheel arrangement may comprise a plurality of wheels for displaying the numbers for a different order of magnitude, respectively. For example, the wheel arrangement may comprise a units wheel and a tens wheel being coupled by an idler wheel. On the other side of at least one wheel there may be arranged a plurality of drive teeth being arranged along the circumferential direction of the respective wheel. The above prolongation of the coupling member is moved over one of these drive teeth when the coupling member is moved from its first position to its second position, thereby bringing the prolongation of the coupling member into engagement with the respective drive tooth. On the other hand, when the metering member is moved backward into its filling position (and the resilient member is thus allowed to discharge), the movement of the coupling member from its second position to its first position caused thereby results in the prolongation of the coupling member rotating the respective wheel by one step, thereby decrementing (or alternatively incrementing) the dose counting unit. At the same time, the coupling member also moves the protective member back into its closed position, and the resilient member returns the inhalation actuated member to its first position and holds it in this position, so that the mark attached to the inhalation actuated member is visible through the respective opening of the casing again. Furthermore by these movements the coupling member is again brought into engagement with the inhalation actuated member, and in particular in this condition the aforesaid arm of the coupling member is held by the inhalation actuated member again. Thereby, the initial condition of the inhalation actuated mechanism and of the device is resumed again, and the above described operation of the powder inhaler can be repeated.

The above mark or flag has a very useful function. It shows a user if he has already taken a dose, thereby removing the possibility of double dosing. Furthermore, only inhaled doses are displayed by the dose counting unit. This reduces wastage and gives the user a true indication of what has been inhaled. The above described dose counting unit is directly driven by a closing operation of the cover. This is more reliable than using a stored energy. However, the driving of the dose counting unit may well be assisted by the stored energy of the resilient member.

The inhalation channel through which air is inhaled in use is preferably designed to comprise a deagglomerator arrangement comprising a substantially tangential air inlet, a preferably rotationally symmetrical vortex chamber, and an air outlet which is axially aligned with the vortex chamber such that airflow within the vortex chamber leads to a strong velocity gradient. The vortex chamber has a diameter d of 6 mm$\leq$d$\leq$10 mm, preferably 6 mm$\leq$d$\leq$8 mm, in particular about 8 mm, since such a diameter dimension has proven to be most effective for the deagglomeration function. The air outlet of the deagglomerator arrangement has preferably a smaller diameter than the vortex chamber. The base section of the vortex chamber may have a substantially elliptical cross-section, while the air outlet (and the inhalation channel) is preferably circular in cross-section. In addition or alternatively, the outer walls of the vortex chamber have the shape of arcs which are non-concentric to the inner diameter of the vortex chamber so as to achieve improved deagglomerator functionality.

Besides the above described features of the powder inhaler of the present invention, a couple of variants could be incorporated into the powder inhaler as well. For example, a manual override mechanism could be incorporated into the inhalation actuated mechanism for manually moving the protective member and manually actuating the inhalation actuated mechanism. This would allow users who could not generate the required flow rate for actuating the inhalation actuated mechanism to manually release the dose contained in the dosing recess and trigger the dose counting unit. Furthermore, an extra part could be added to override the inhalation actuated dose counting unit. This would especially be of benefit to those people who cannot achieve the required flow rate to operate the inhalation actuated mechanism. Furthermore, a one-way valve could be placed in the inhalation channel, preferably over the inlet to the deagglomerator arrangement (cyclone). This could reduce any moisture blown into the inhaler by about 50%.

Furthermore, another means of delivering a dose upon inhalation could be incorporated. Such a means could comprise a resilient member, in particular in the form of a spring, which is compressed by means of opening the cover. The resilient member would act on the metering member. The metering member would be free to move to a half-way position between the container and the inhalation channel. However, the metering member would be held at this half-way position until an inhalation actuated mechanism releases the metering member to complete its travel to the inhalation channel and, hence, present the dose contained in the dosing recess for inhalation. The half-way position (midpoint position) would have the combined effect of retaining the dose in the dosing recess and protecting it from moisture from user exhalation or discharge.

The device of the present invention delivers consistent respirable dose values to the patient across a wide range of pressure drops. For example, between 30 l/min and 90 l/min the fine particle fraction, a measure of Pulmonary penetration varies by less than 20%. Furthermore, this performance only requires a low work input from the patient with the device being classified as a low to medium resistance device.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope.

FIGS. 23A-C show a rear view, a perspective view, and a front view of a tens wheel of the dose counting unit.

DETAILED DESCRIPTION OF THE PREFERRED EMBODIMENTS

Figure 1:
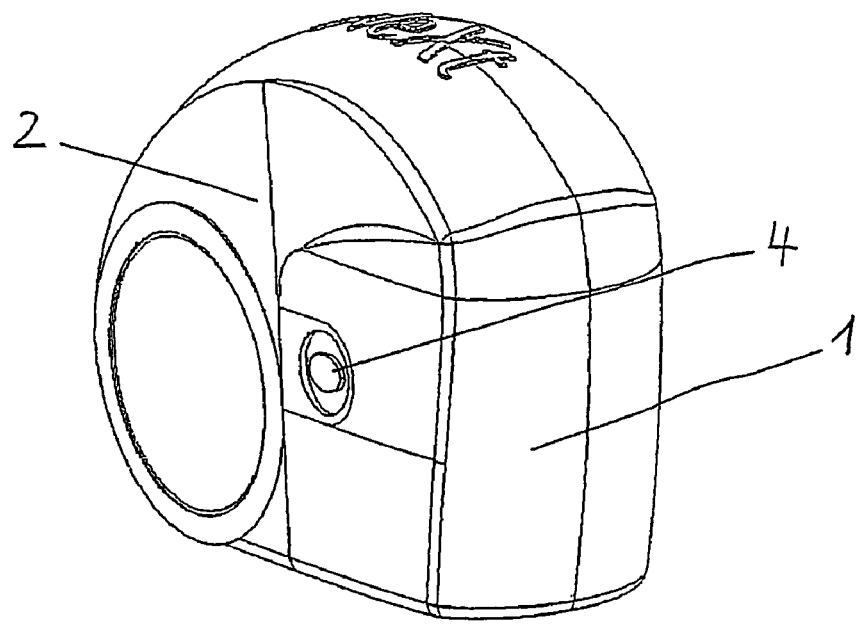
FIG. 1 shows a perspective outside view of a powder inhaler according to a preferred embodiment of the present invention.

The powder inhaler shown in FIG. 1 comprises a casing with a lower shell 1 and an integral cover 2 being pivotably or rotatably coupled to the lower shell 1. In a side surface of the lower shell 1 a window 4 is formed for displaying numbers of a dose counting unit which will be described later.

Figure 2:
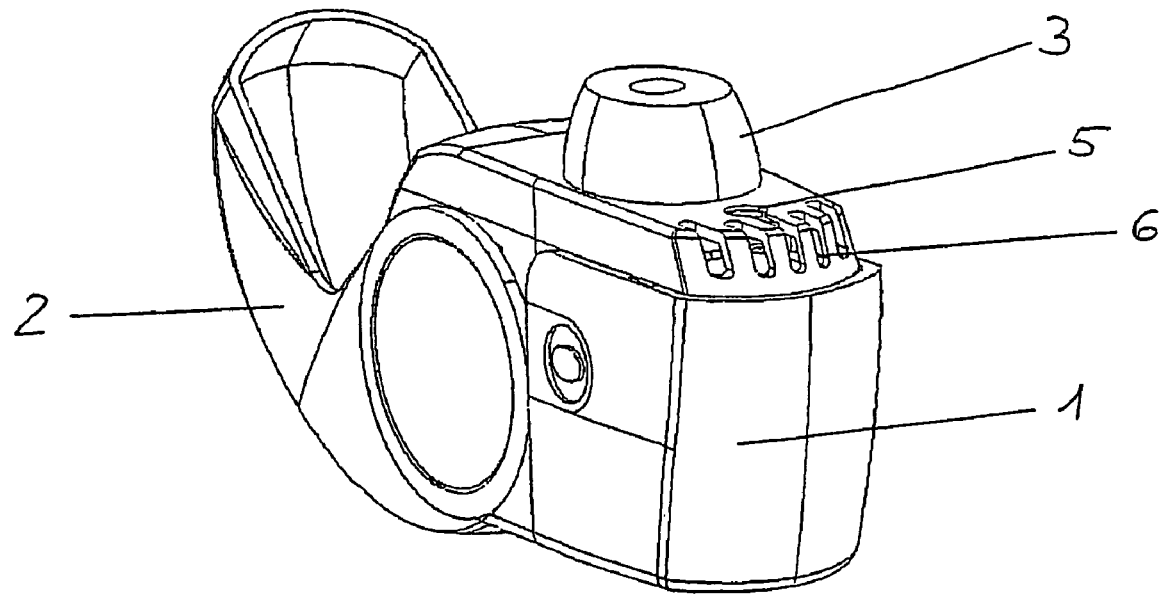
FIG. 2 shows a perspective view of the powder inhaler when a cover thereof is opened.

As can be taken from FIG. 2, the integral cover 2 can be opened to reveal a mouthpiece 3 with which a user can inhale a powdered medicament. At the upper front side of the mouthpiece 3 slots 6 are formed which allow air inlet. Furthermore, at the upper side of the mouthpiece 3 an opening or a hole 5 is formed which allows to view a visible mark or flag showing if a dose is ready. As will be described later, this flag disappears upon inhalation showing that the respective dose has been taken.

Figure 3:
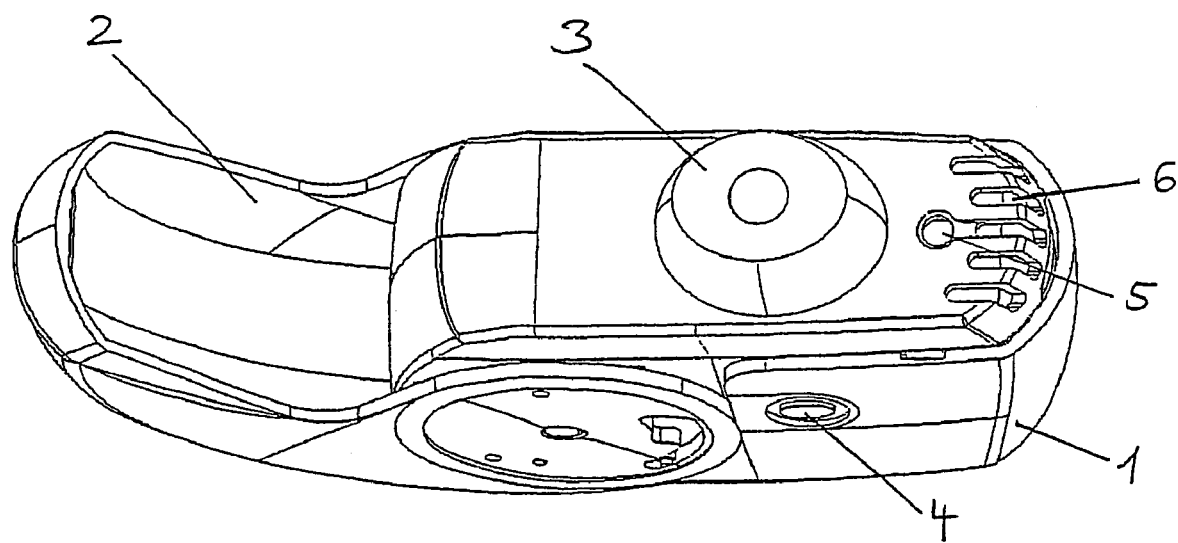
FIG. 3 shows a top view of the powder inhaler when the cover is opened.
Figure 8:
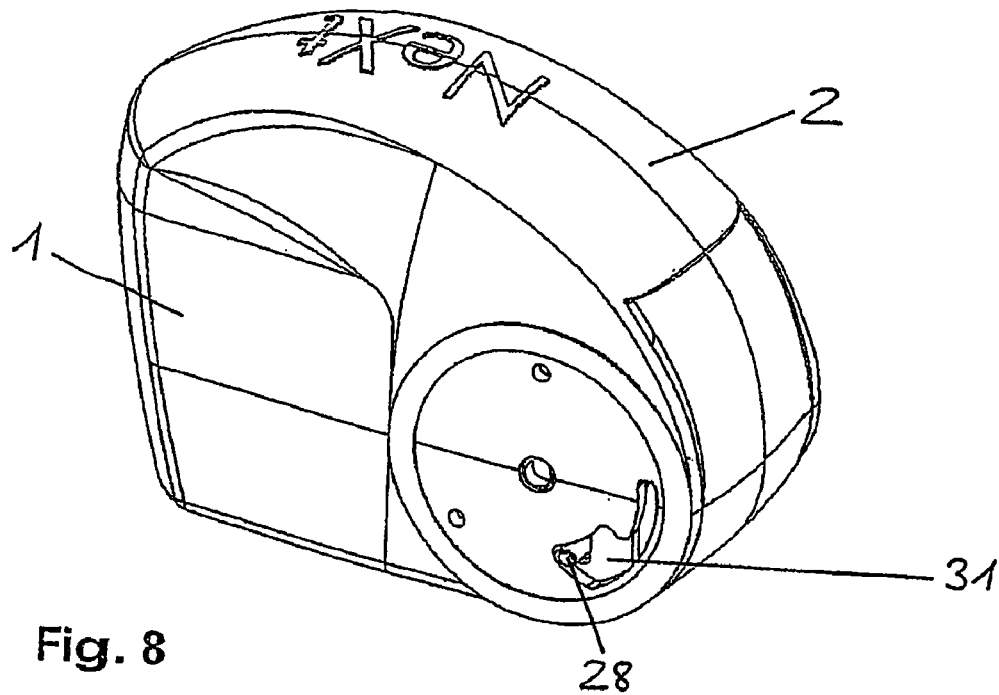
FIG. 8 shows a perspective side view of the powder inhaler without side labels when the cover is closed.

The structure of the lower shell 1, the integral cover 2 and the mouthpiece 3 can also be taken from FIG. 3 which shows a top view of the powder inhaler. In FIG. 3 (and in FIG. 8), the integral cover 2 is shown without side labels which are depicted in FIGS. 1 and 2. These side labels prevent access to profiled cam tracks being described later so as to protect these cam tracks from dust etc.

Figure 13:
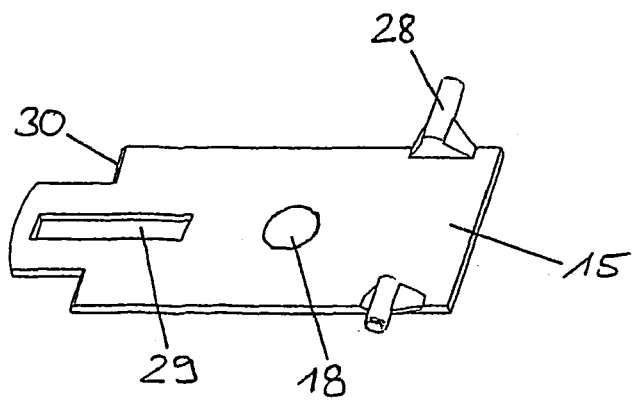
FIG. 13 shows a perspective view of a slide of the powder inhaler.
Figure 14:
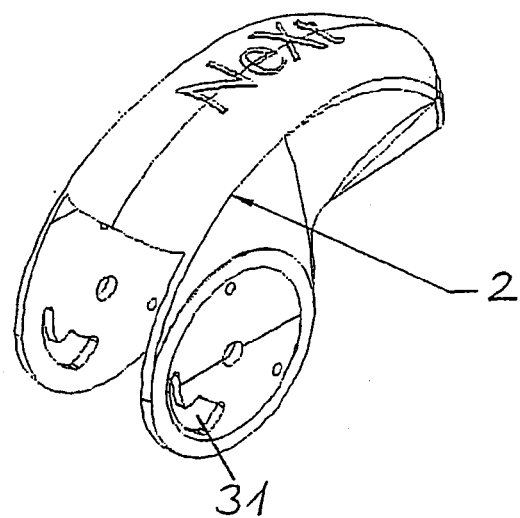
FIG. 14 shows a perspective view of the cover of the powder inhaler.
Figure 15:
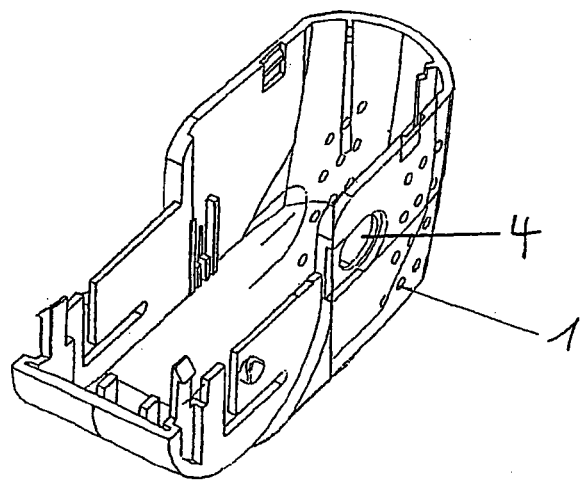
FIG. 15 shows a perspective view of a part of a casing of the powder inhaler.
Figure 16:
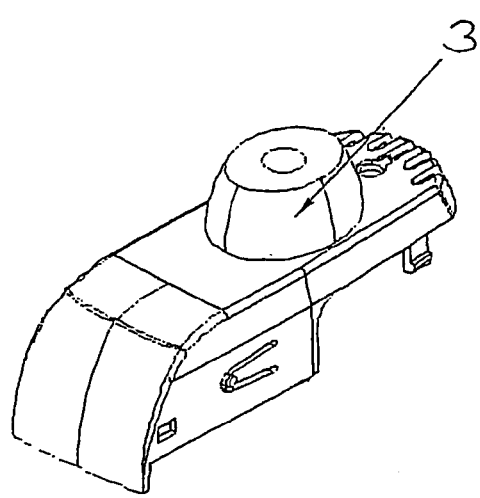
FIG. 16 shows a perspective view of a mouthpiece of the powder inhaler.

FIG. 14, FIG. 15, and FIG. 16 show perspective views of the integral cover 2, the lower shell 1, and the mouthpiece 3, respectively. The lower shell 1 and the mouthpiece 3 are constructed such that the mouthpiece 3 can be snap-fitted onto the lower shell 1. From both side surfaces of the lower shell 1 projections or bolts extend which engage with respective central openings at both side surfaces of the integral cover 2, thereby allowing rotational movement of the integral cover 2 relative to the lower shell 1. As can be seen from FIG. 1 and FIG. 2, the integral cover 2 is closed when its lower surface rests on the upper rim of the lower shell 1, and the integral cover 2 can be opened until its rear edge abuts against the underside of the lower shell 1 (see FIG. 2). At both side surfaces of the integral cover 2, openings 31 having the shape of profiled cam tracks are formed which are coupled to side projections 28 of a shuttle or slide 15, a perspective view thereof being shown in FIG. 13. This kind of coupling between the integral cover 2 and the slide 15 will be described later in detail.

Within the casing and the lower shell 1, respectively, there are two sub-assemblies arranged. The first sub-assembly is a dosing sub-assembly 13 which in particular meters a powdered medicament, while the second sub-assembly is a dose counting sub-assembly 14 which comprises an inhalation actuated mechanism and a dose counting unit for counting the number of doses taken by the user.

Figure 4:
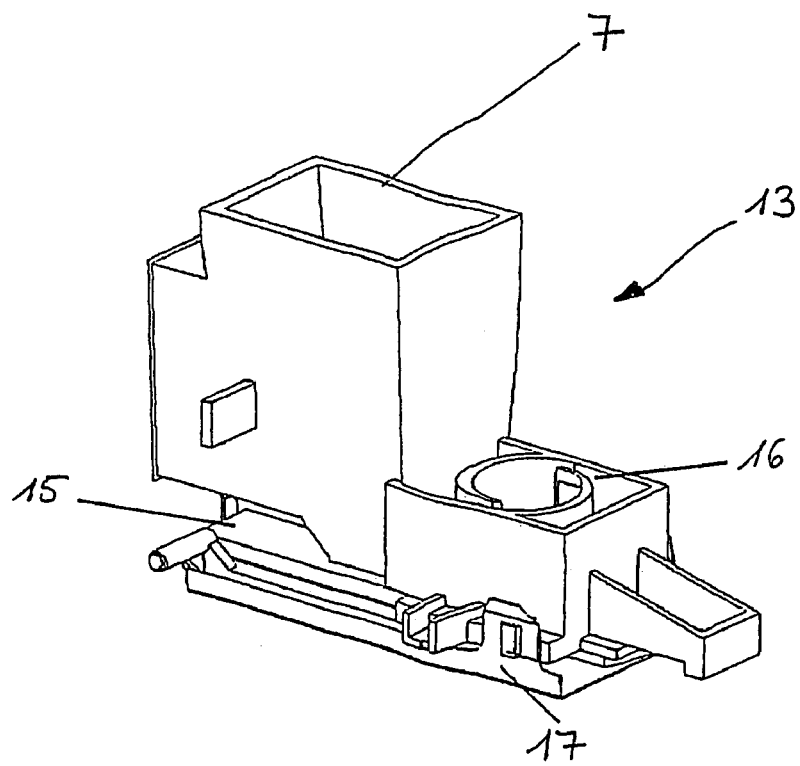
FIG. 4 shows a perspective view of a dosing sub-assembly of the powder inhaler.

FIG. 4 shows a perspective view of the dosing sub-assembly 13. As can be seen, the dosing sub-assembly 13 comprises a container or a reservoir 7 for storing a powdered medicament, the above-mentioned slide 15 shown in FIG. 13, and a deagglomerator arrangement 16 to be coupled to an inhalation channel of the mouthpiece 3. A spring 17 is clamped onto side projections of the dosing sub-assembly 13 such that it holds the dosing sub-assembly together.

Figure 18:
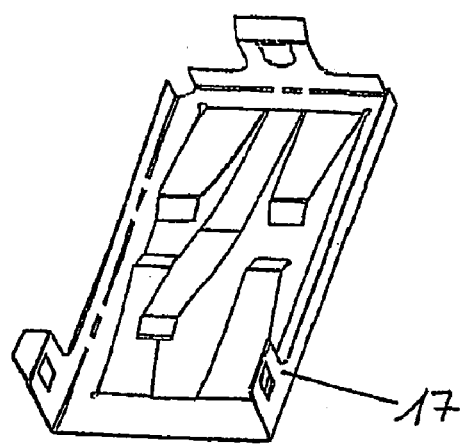
FIG. 18 shows a perspective view of a slide spring of the powder inhaler.

FIG. 18 shows a perspective view of the spring 17. As can be easily seen, the spring 17 comprises four resilient side spring members, two spring members being fixed to the rear side and two spring members being fixed to the front side of the spring 17. All four spring members extend in the longitudinal direction of the spring 17 such that their free ends are arranged in a middle portion of the spring 17. These spring members apply a force to the slide 15 such that the slide 15 is continuously urged against the underside of the dosing sub-assembly 13. From the rear side to the front side of the spring 17, there extends an additional resilient spring member which applies a separate force to the longitudinal middle region of the slide 15. As is shown in FIG. 13, in this longitudinal middle region the slide 15 has a dosing recess 18 in the form of a dosing cup for metering a dose of the powdered medicament and for transporting the dose from a filling position underneath the container 7 to an inhalation position underneath the deagglomerator arrangement 16. The above-mentioned separate spring member extending along the longitudinal middle region of the spring 17 ensures that the dosing recess 18 is reliably pressed against the underside of the dosing sub-assembly 13 if the slide 15 is in its inhalation position so that the dosing recess 18 is properly located under the deagglomerator arrangement 16.

Figures 6A, 6B:
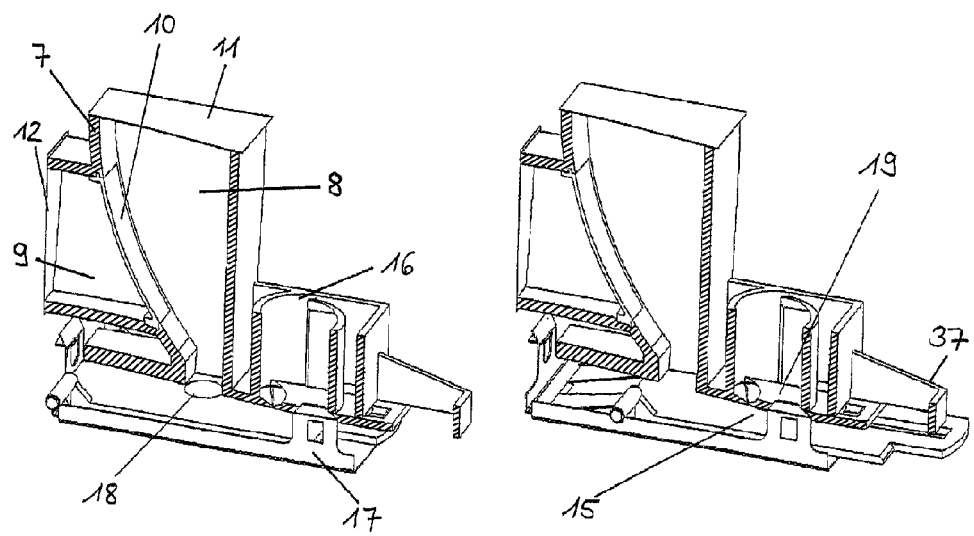
FIGS. 6A and 6B show cross-sectional views of the dosing sub-assembly.

As already indicated above, the slide 15 serves as a metering member which can be moved in the horizontal direction from a filling position shown in FIG. 6A to an inhalation position shown in FIG. 6B. Thus, the slide 15 is slidingly moveable between the filling position, where the dosing recess 18 is located underneath a dosing opening of the container 7 and faces the dosing opening, and the inhalation position, where the dosing recess 18 is located underneath and faces an inhalation opening of the deagglomerator arrangement 16 which is in communication with an inhalation channel (to be described later) of the mouthpiece 3.

As is shown in FIG. 6A, the container 7 is a container with integral desiccant. The container 7 comprises a medicament chamber 8 storing a powdered medicament and a desiccant chamber 9 storing a desiccant for absorbing moisture that may have entered the medicament chamber 8. The desiccant chamber 9 is separated from the medicament chamber 8 by a separate permeable membrane 10. This permeable membrane 10 is of a different permeability than the permeability between either the desiccant or the medicament to the outside world. The permeability of the membrane 10 can be achieved, for example, by making it of a different material and/or a thinner section than the main body of the container 7. Foils 11, 12 are used to seal both the medicament chamber 8 and the desiccant chamber 9. As a matter of course, other suitable sealing means may be used for sealing both chambers 8, 9 as well.

The above described integral desiccant system has the following advantages. The desiccant has only to dry out the medicament chamber rather than the whole device. This requires less desiccant reducing product size and cost. Furthermore, the desiccant is always sealed. This means that the desiccant will still be effective even if the cover is left open. The desiccant is stored in the separate sealed desiccant chamber 9. This reduces the risk of incorrect assembly if the desiccant used the same closure as the medicament. Moreover, the integral container 7 comprising both the medicament chamber 8 and the desiccant chamber 9 can be manufactured using a 2-shot moulding. This ensures a good seal between the medicament chamber 8 and the desiccant chamber 9 at low product cost. Finally, the foil sealing provides a tamper-proof means of filling the device with the medicament or drug which has a very low permeability and requires only little product space.

As is shown in FIG. 6A and FIG. 6B, the medicament chamber 8 has a gradually decreasing cross-section diameter from its top to its bottom so that the medicament chamber 8 is shaped like a funnel supporting an easier filling of the dosing recess 18 through the dosing opening formed in the bottom of the medicament chamber 8.

The powder inhaler shown in the drawings solves many technical problems that may occur throughout the life cycle of the powder inhaler. The fundamental operating sequence of the powder inhaler is to open the integral cover 2, inhale the dose of the powdered medicament, and close the integral cover 2.

The cover 2 is gripped by the user and opened. As already described above, the projections 28 formed at both longitudinal sides of the slide 15 (see FIG. 13) engage with the respective side openings 31 formed at both sides of the cover 2. In particular, these side openings 31 are profiled cam tracks. The coupling between the profiled cam tracks 31 and the projections 28 is such that opening of the cover 2 causes the slide 15 to move forward from its filling position (FIG. 6A) to its inhalation position (FIG. 6B). Likewise, closing of the cover 2 causes the slide 15 to move from its inhalation position backward to its filling position again. That is to say, by opening/closing the cover 2, the slide 15 is moved substantially linearly with respect to the casing. In particular, the profiled cam tracks 31 are shaped such that opening of the cover 2 by a predetermined first angle, for example, by an angle of about 30°, from its closed position does not actuate the slide 15. That is the first 30° of the movement of the cover 2 is slack where no mechanism is driven. The industrial design of the powder inhaler is intended to convey the correct orientation of use. Furthermore, the coupling between the cover 2 and the slide 15 is such that the slide 15 is properly moved to its inhalation position already a predetermined second angle, prior to the cover 2 being fully opened. For example, the slide 15 may be moved to its inhalation position already when the cover 2 has been opened by 90°. In a range of 90°-135°, e.g., there is again free play. Therefore, the dose of the powdered medicament filled in the dosing recess 18 is correctly presented to the deagglomerator arrangement 16 as well as the respective inhalation channel coupled thereto, ready for inhaling, 90°-45° prior to the cover 2 being fully open (An opening angle of 180° is considered as representing a fully open position of the cover). This ensures that the dose will be ready prior to the mouthpiece 3 becoming exposed to the user if the user should attempt a discrete operation of the powder inhaler, for example. There is an audible click indicating that the cover 2 is fully open.

When the cover 2 is closed, there are for example 45° of free play before a further closing of the cover 2 moves the slide 15 from the inhalation position to the filling position. Before the cover 2 is completely closed, there may be 15° of free play, for example. It should be noted that the profiled cam tracks 31 shown in the drawings are only exemplary.

As already mentioned before, the dosing recess 18 has the shape of a dosing cup which is designed to maximize the accuracy of gravitationally filling the dosing cup and maximize the ease of airborne entrainment of the formulation upon inhalation. The dosing cup is circular in profile (in top view) with a semi-elliptical cross-section (i.e. the cross-section has the shape of the half of an ellipse); the diameter being three times the depth. This enables the cyclonic airflow in the airway of the deagglomerator arrangement 16 to scour the dosing cup 18 effectively. The circular profile and the above-mentioned ratio of depth to top area also combine the lowest variability of filling and scraping upon leaving the container 7.

During opening the slide 15 is moved from the filling position to the inhalation position as well as after the slide 15 has reached its inhalation position, the dose of the powdered medicament filled in the dosing recess 18 of the slide 15 is prevented from falling out by a protective member, i.e. a dose protector 19. The dose protector 19 is arranged slidingly moveable on the slide 15 between a closed position and an open position. In its closed position, the dose protector 19 at least completely covers the dosing recess 18 when the slide 15 is in the inhalation position; while in its open position the dose protector 19 exposes the dosing recess 18 to the deagglomerator arrangement 16 and the inhalation channel when the slide 15 is in its inhalation position. The dose protector 19 is held in its closed position by an inhalation or breath actuated mechanism which will be described later. This inhalation actuated mechanism is constructed such that the dose protector 19 is moved from its closed position to its open position only if the inhalation suction force affected by the user in the inhalation channel exceeds a predetermined level. Furthermore, the inhalation actuated mechanism is arranged such that only an inhalation suction breath not a blowing breath can actuate the inhalation actuated mechanism and cause a movement from the dose protector from its closed position to its open position.

In the following, the inhalation actuated mechanism in combination with the dose protector and the dose counting unit is described in detail.

Figures 5A, 5B:
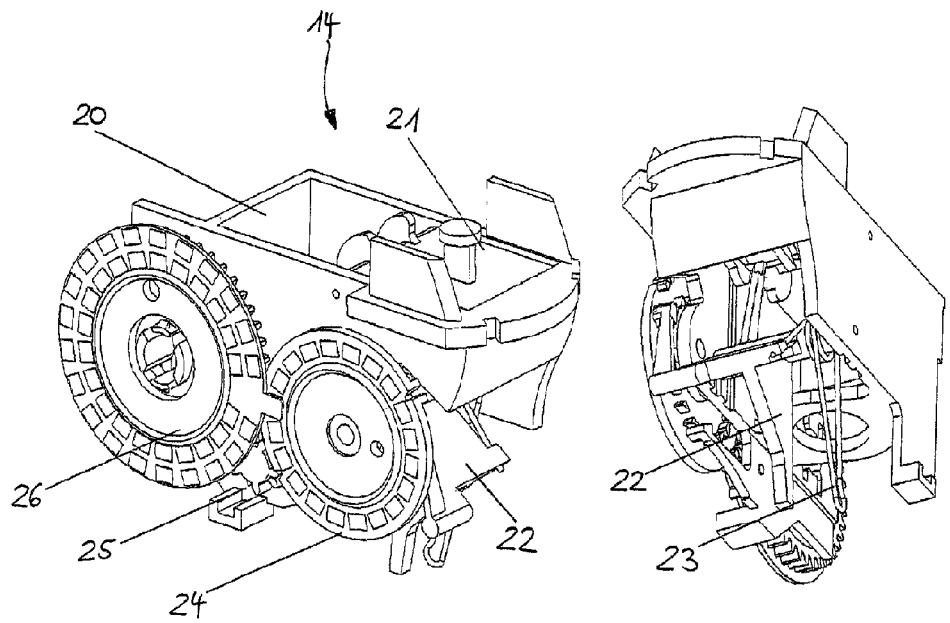
FIGS. 5A and 5B show perspective views of a dose counting sub-assembly of the powder inhaler.

FIG. 5A and FIG. 5B show perspective views of the dose counting sub-assembly 14 already mentioned above. The dose counting sub-assembly 14 consists of a sub-frame 20 which holds a flap 21 acting as an inhalation actuated member, a yoke 22 acting as a coupling member and a drive spring 23 acting as a resilient member. The drive spring 23 drives the dose counting unit which, in the present case, comprises a units wheel 24 and a tens wheel 26 being coupled by an idler wheel 25. Furthermore, the drive spring 23 drives the dose protector 19. The units wheel 24 and the tens wheel 26 display the number of doses remaining in the medicament chamber 8. As a matter of course, the drive spring 23 may be replaced with a resilient means being constituted by a plurality of spring elements or spring parts, for example.

Figure 7A:
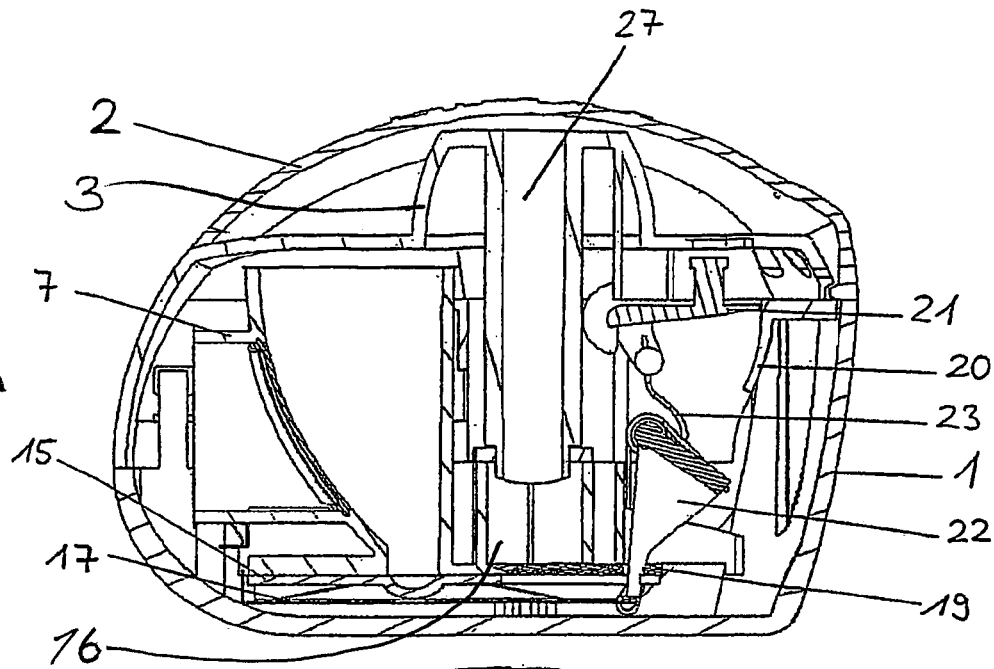
FIGS. 7A and 7B show cross-sectional side views of the powder inhaler when the cover is closed.
Figure 7B:
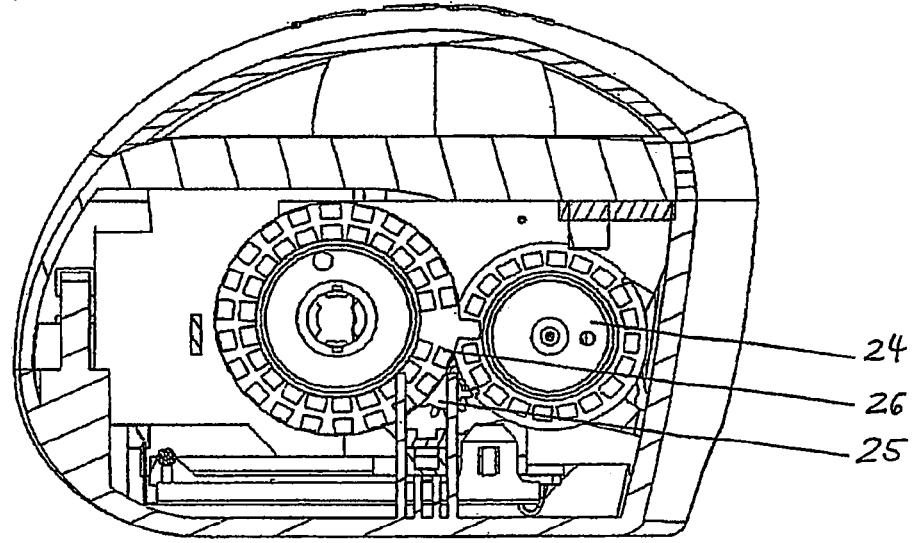

In FIG. 7A and FIG. 7B partial cross-sectional views of the whole powder inhaler along different cross-sectional lines with the cover 2 being closed are shown. In particular, from FIG. 7A it can be seen that the mouthpiece 3 comprises the inhalation channel 27 extending from the upper side of the mouthpiece 3 downward so as to be coupled to the deagglomerator arrangement (cyclone) 16 of the dosing sub-assembly 13.

The functionality of the inhalation actuated mechanism as well as the dosing counting unit is as follows.

Figure 9:
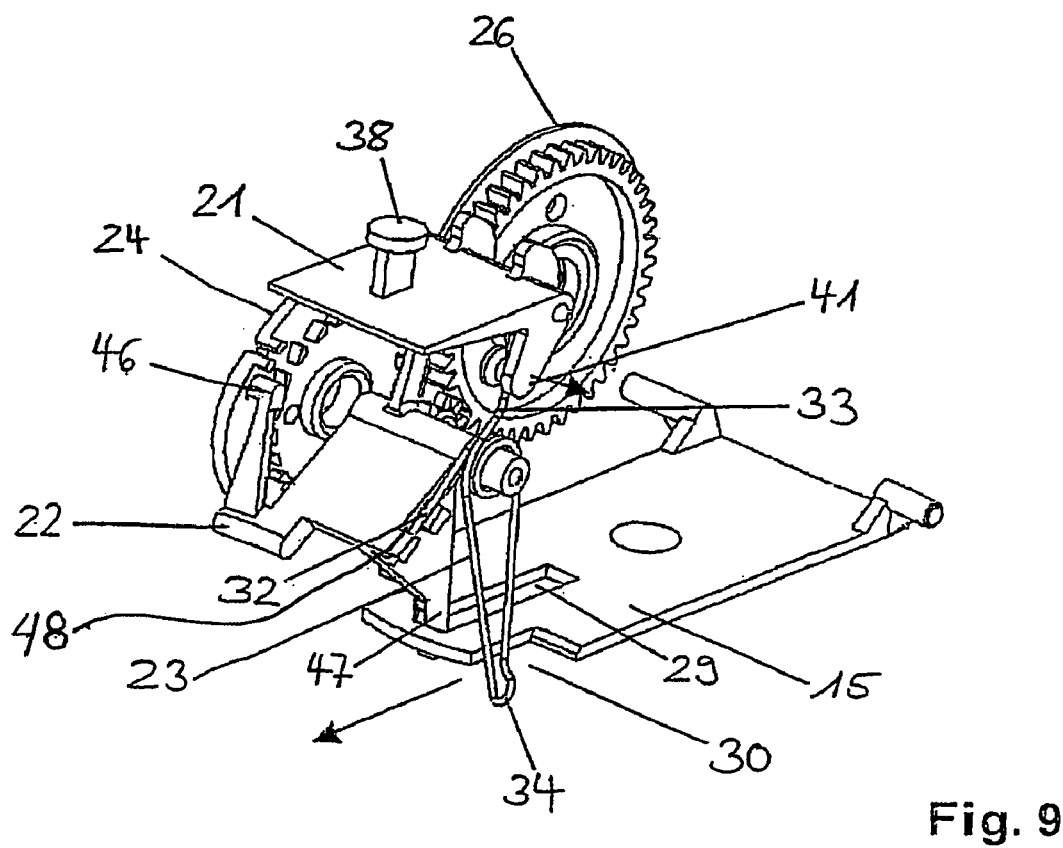
FIG. 9 shows a perspective view of an inhalation actuated mechanism and a dose counting unit of the powder inhaler.

As shown in FIG. 9, there are formed recesses 30 at both front corner portions of the slide 15. At one of these recesses 30, a prolonged end 34 of the drive spring 23 engages with the slide 15 if the slide 15 is moved forward. By the contact with the slide 15, the drive spring 23 of the inhalation actuated mechanism is tensioned and charged up. A first end 33 of the drive spring 23 rests at a portion 41 of the flap 21 when the drive spring 23 is in its discharged state. Therefore, by charging up the drive spring 23 this reset force exerted by the first end 33 of the drive spring 23 on the flap 21, normally holding the flap 21 in a first horizontal position shown in FIG. 9, is released.

Figure 19A:
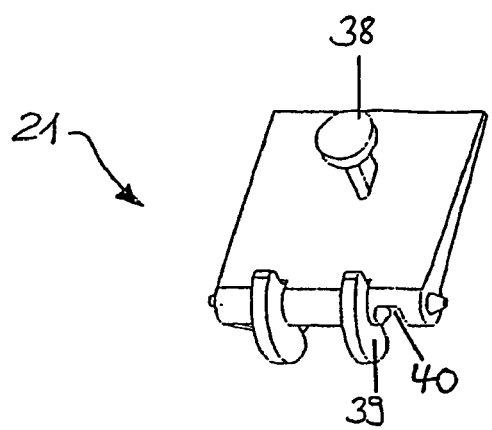
FIGS. 19A-C show a perspective view, a cross-sectional view, and a front view of an inhalation actuated member of the inhalation actuated mechanism.
Figure 19B:
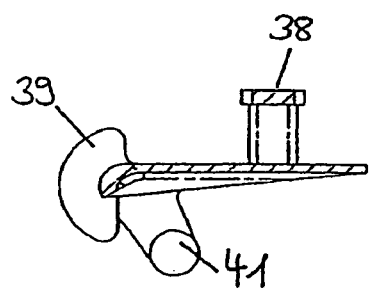
Figure 19C:
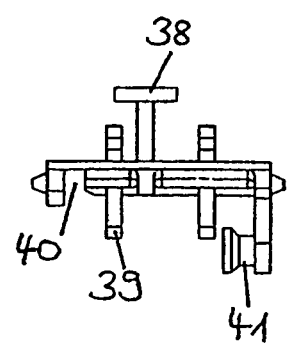

FIGS. 19A-C show different perspective views of the flap 21. As can be seen, at the upper surface of the flap 21, a flag 38 is formed which acts as a mark being visible through the opening 5 in the mouthpiece 3 when the flap 21 is in its first horizontal position, whereby indicating that a dose is ready for inhalation. Furthermore, the flap 21 comprises a feature 40 for engagement with an arm 43 of the yoke 22. Finally, the flap 21 also comprises two projections 39 which act as a counterweight. This counterweight balances the flap 21 reducing not only the actuation force required but also the susceptibility of the mechanism to accidental triggering.

Figure 21:
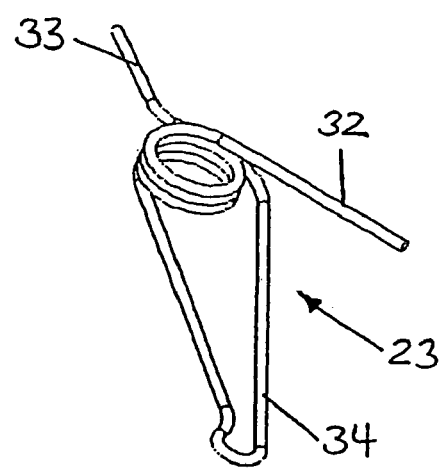
FIG. 21 shows a perspective view of a resilient member of the inhalation actuated mechanism.

As shown in FIGS. 9 and 21, the drive spring 23 has a second end 32 which rests on a lateral side surface 48 of the yoke 22.

Figure 25A:
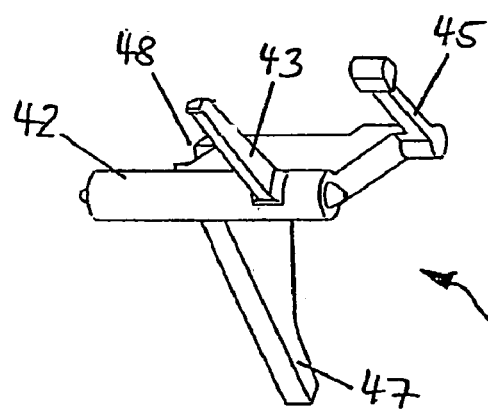
FIGS. 25A-B show a perspective view and a side view of a coupling member of the inhalation actuated mechanism and the dose counting unit.
Figure 25B:
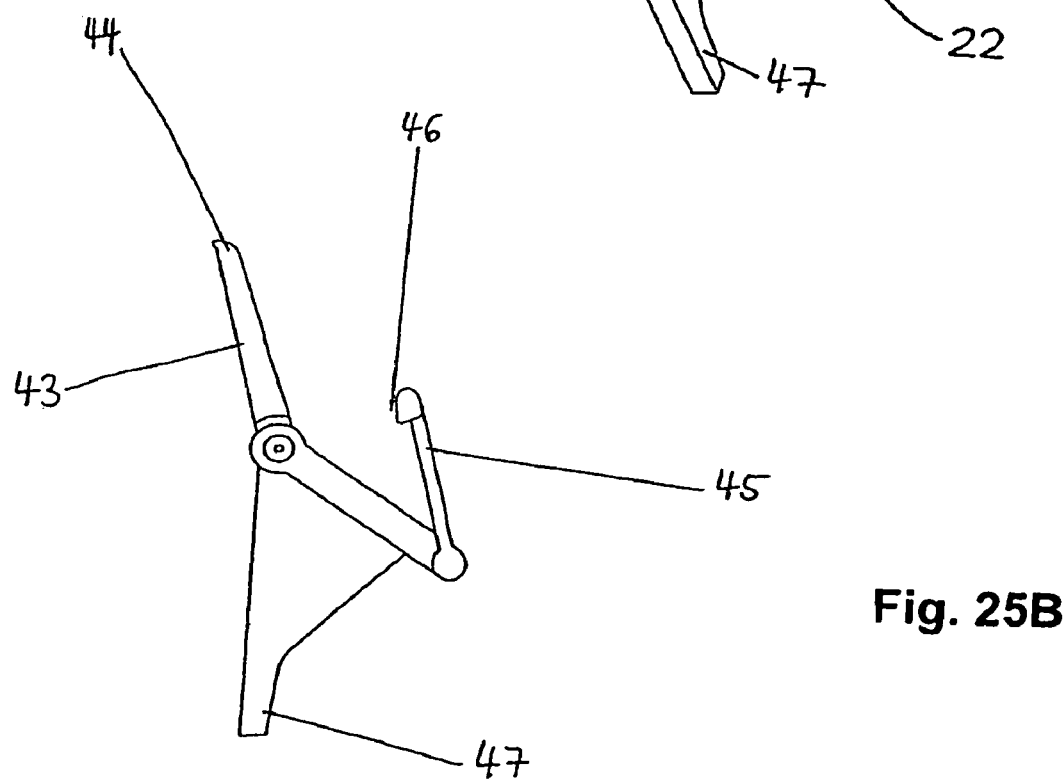

FIGS. 25A-B show a perspective view and a side view of the yoke 22. The yoke 22 has a shaft-like portion 42 on which the drive spring 23 is mounted. Furthermore, in FIGS. 25A-B the arm 43 is depicted whose upper end 44 is retained and released, respectively, by the flap 21. At that lateral side of the yoke 22 which is opposite to the lateral side surface 48 on which the second end 32 of the drive spring 23 rests, there is formed a projection 45 having a thickening 46 at its end for operating the dose counting unit which will be described later. From the bottom of the yoke 22, there extents a prolongation 47 which engages, on the one hand, with an opening 36 formed in the dose protector 19 and, on the other hand, with a slit 29 formed in the front end portion of the slide 15 (see FIG. 13 and FIG. 20).

As already described above, when the drive spring 23 is decompressed and discharged, its end 33 exerts a reset force on the portion 41 of the flap 21, thereby holding the flap 21 in its first horizontal position, as shown in FIG. 9. In this condition, the dose protector 19 prevents the powdered medicament contained in the dosing recess 18 from being displaced from the deagglomerator arrangement 16 (cyclone) if the user blows into the mouthpiece 3. Furthermore, the flap 21 provides a resistance if the user blows into the device giving positive feedback.

If, however, the slide 15 is pushed forward by opening the cover 2, thereby compressing and charging the drive spring 23, the reset force exerted by the end 33 of the drive spring 23 on the flap 21 is released, and the flap 21 can be rotated from its first horizontal position shown in FIG. 9 into a second position being pivoted relative to the first position if there is a sufficient high inhalation suction force effected by the user in the inhalation channel 27 of the powder inhaler.

Figure 10:
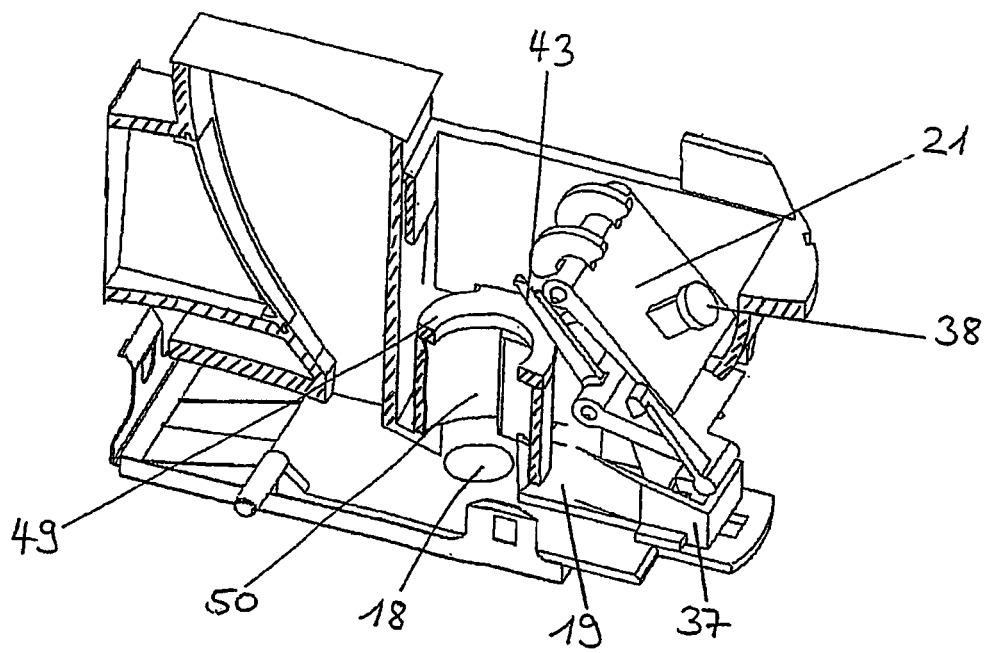
FIG. 10 shows a partial cross-sectional view of the inner construction of the powder inhaler upon inhalation.
Figure 11:
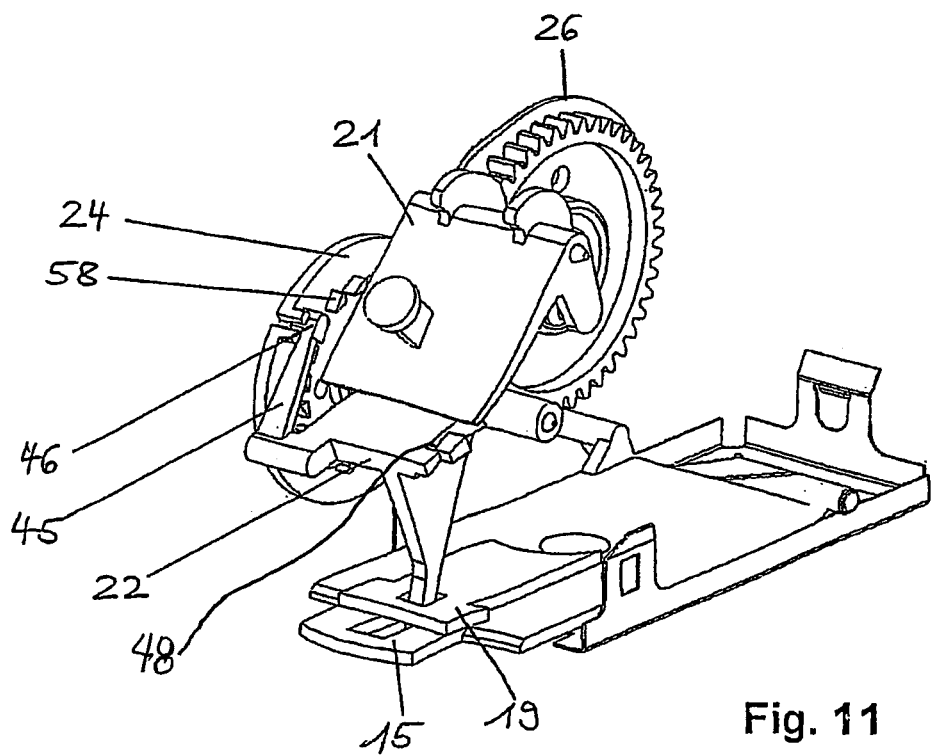
FIG. 11 shows a perspective view of the inhalation actuated mechanism and the dose counting unit of FIG. 9 upon inhalation.

In the latter case, the flap 21 is moved by this sufficient high inhalation force from its first position shown in FIG. 9 into its second position shown in FIG. 10. As can be also seen from FIG. 10, by this movement of the flap 21 the arm 43 of the yoke 22 is released. This enables the drive spring 23, due to its compression, to move its second end 32, which is in engagement with the lateral side surface 48 of the yoke 22, and thus the yoke 22 slightly upward. By this rotational upward movement of the yoke 22 the prolongation 47 extending from the upper side of the yoke 22 is moved forward, thereby moving the dose protector 19 from its closed position to its open position. This situation is shown in FIG. 10 as well as in FIG. 11.

Figure 20:
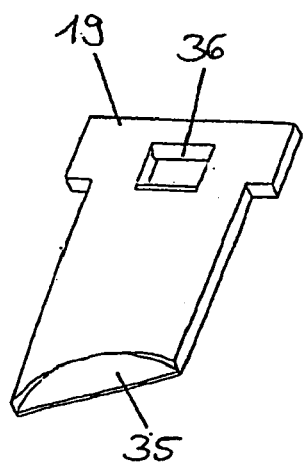
FIG. 20 shows a perspective view of a protective member of the powder inhaler.

In FIG. 20, a perspective view of the dose protector 19 is shown. In particular, in FIG. 20 the opening 36 is shown which is in engagement with the prolongation 47 extending downwardly from the bottom of the yoke 22. The front end 35 of the dose protector 19 has a partial circular or semicircular shape so that it can form part of the wall of the deagglomerator arrangement or cyclone 16 when the dose protector 19 is in its closed position.

Since the dose protector 19 has been moved out from its closed position into its open position by the yoke 22, the dosing recess 18 of the slide 15 is exposed to the inside 50 of the cyclone, and the dose of the powdered medicament contained in the dosing recess 18 can be inhaled through the cyclone and the inhalation channel 27 as well as the mouthpiece 3. In the cyclone, the drug or the powdered medicament is entrained into a swirling airflow where the active part of the formulation is disaggregated from the carrier (see reference sign 49).

Furthermore, since the flap 21 has been moved from its first horizontal position (see FIG. 9) to its second position rotated or pivoted relative to its first position (see FIGS. 10 and 11), the flag 38 formed at the upper surface of the flap 21 is no longer visible through the opening 5 in the upper side of the mouthpiece 3. That is the flag 38 has disappeared thereby indicating that a dose has been taken, and a new dose is not ready for inhalation again, yet.

Figure 17:
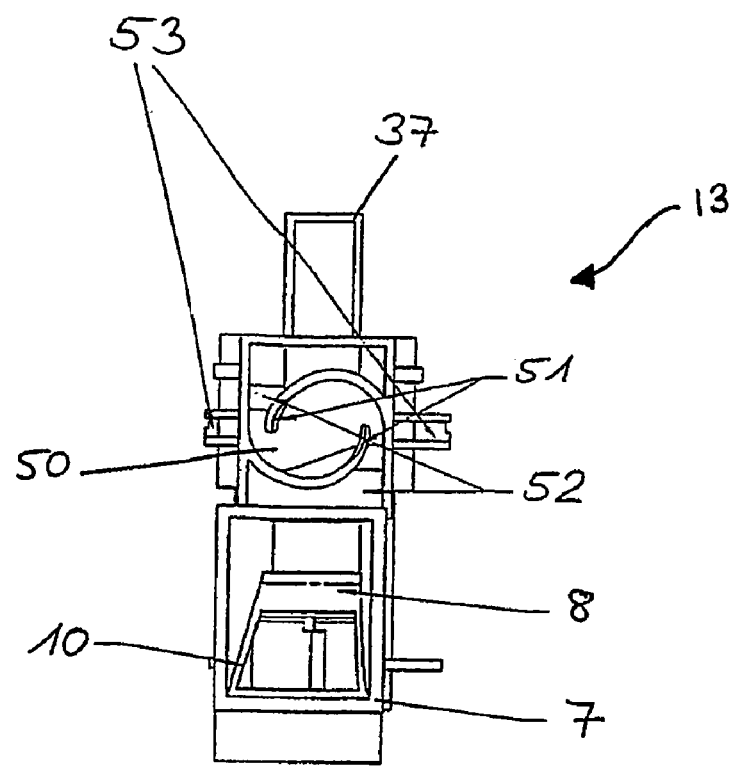
FIG. 17 shows a top view of the dosing sub-assembly shown in FIGS. 6A and 6B.

FIG. 17 shows a top view of the dosing sub-assembly 13, depicting the inside 50 of the cyclone 16 as well as portions 51 (corresponding to side walls 78 depicted in FIG. 26) which allow the mouthpiece to be assembled, portions 52 which produce a cyclonic airflow within the cyclone, and projections 53 for mounting the dosing sub-assembly 13 within the lower shell 1 of the powder inhaler. Furthermore, in FIG. 17 there is also depicted the end stop 37 for the prolongation 47 of the yoke 22 and the dose protector 19, respectively.

In the following, the functionality of the dose counting unit is explained in detail. As already mentioned above, the dose counting unit, being provided for counting the number of doses taken (up counter) or, alternatively, the number of doses remaining in the container (down counter), comprises the units wheel 24 and the tens wheel 26 being coupled to one another by the idler wheel 25.

Figure 22A:
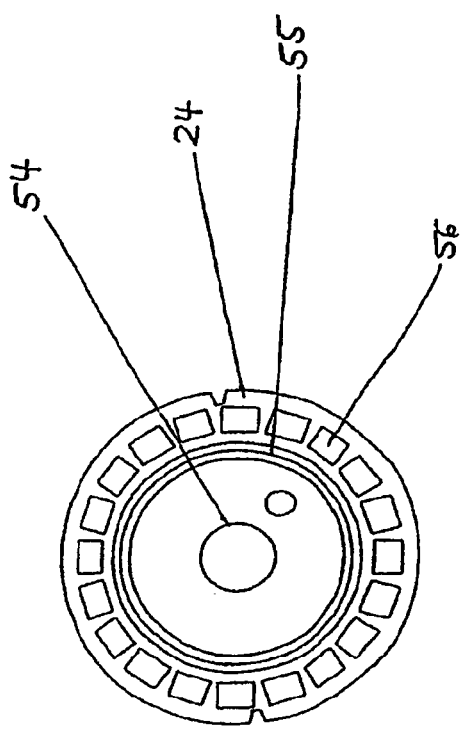
FIGS. 22A-C show a front view, a perspective view, and a rear view of a units wheel of the dose counting unit.
Figure 22B:
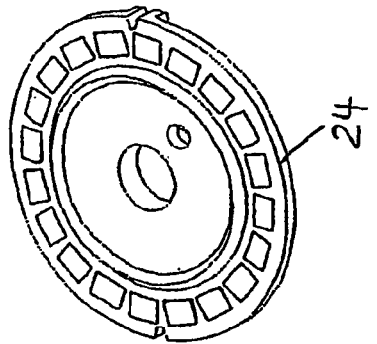
Figure 22C:
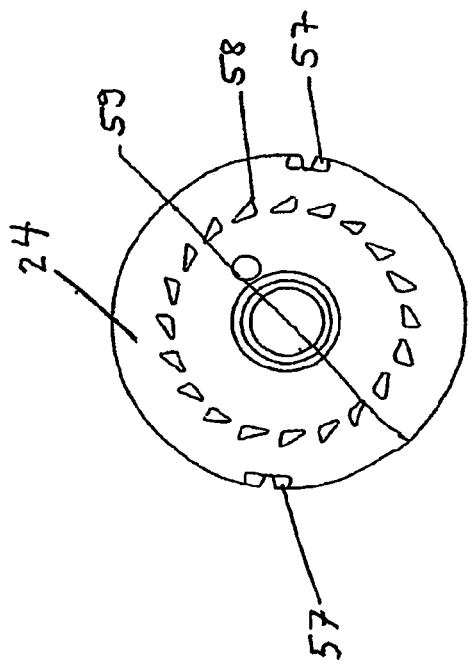

FIGS. 22A-C show a front view, a perspective view, and a rear view of the units wheel 24. The units wheel 24 comprises a central opening 54 at which it is rotatably mounted at the dose counting sub-assembly 14 inside the casing of the powder inhaler as shown in FIGS. 5A and 5B, for example. Reference sign 55 designates a feature which provides a thrust-bearing surface with the lower shell 1. Reference sign 56 designates numbers which are printed on the outer surface of the units wheel 24 along the circumferential direction thereof and with equal intervals therebetween. At the outer periphery of the units wheel 24, there are formed teeth 57 for driving the idler wheel 25. As can be taken from the rear view 22C of the units wheel 24, these teeth 57 are formed diametrically opposed to each other. Finally, on the back of the units wheel 24 there are drive teeth 58 which are brought into engagement with the projection or cantilever 45 of the yoke 22 so as to drive the units wheel 24 step by step upon completion of an inhalation process. As can be easily seen from FIGS. 22A-C, the drive teeth 58 each are inclined in the circumferential direction of the units wheel 24. For example, the diameter 59 of the units wheel 24 may be about 20 mm.

FIGS. 23A-C show a rear view, a perspective view and a front view of the tens wheel 26. On the back of the tens wheel 26, there is formed a plurality of teeth 62 in the circumferential direction of the tens wheel 26. These teeth 62 are driven by the idler wheel 25. Reference numeral 60 designates missing teeth which prevent a drive of the tens wheel 26 when the medicament chamber 8 is empty, that is the tens wheel 26 is constructed such that during one life cycle of the powder inhaler nearly one complete rotation of the tens wheel 26 is effected by the dose counting unit. Reference numeral 61 designates an end stop with the casing of the powder inhaler. The diameter 63 of the tens wheel 26, for example, may be about 25 mm. Reference numeral 64 designates an opening at which the tens wheel 26 is rotatably mounted at the dose counting sub-assembly 14, as shown in FIGS. 5A and 5B, for example. Reference numeral 65 designates a feature which provides a thrust-bearing surface with the casing of the powder inhaler. Furthermore, reference numeral 66 designates a feature which provides a thrust-bearing surface with the lower shell 1, and reference numeral 67 designates the periphery of the opening 64 which is located on the casing of the powder inhaler. On the outer surface of the tens wheel 26, there are formed two circumferential rows of numbers 68. These two rows of numbers display tens and hundreds numbers in correct orientation. In each case, a combination of a units number of the units wheel 24 with a tens number and a hundreds number of the tens wheel 26 is visible through the opening 4 formed in the lower shell 1 of the powder inhaler (see FIG. 1, for example). Each such combination of horizontally adjacent numbers of the units wheel 24 and the tens wheel 26 designates a corresponding number of doses remaining in the medicament chamber 8. Finally, at the outer periphery of the tens wheel 26, there is also formed a projection 69. Along the radial direction of this projection 69, there are no tens and hundreds numbers formed on the outer surface of the tens wheel 26, and this projection 69 covers the units wheel 24 if the medicament chamber 8 is empty such that no numbers are visible through the opening 4 of the lower shell 1, thereby indicating to the user that there is no dose remaining in the medicament chamber any more.

Figure 24:
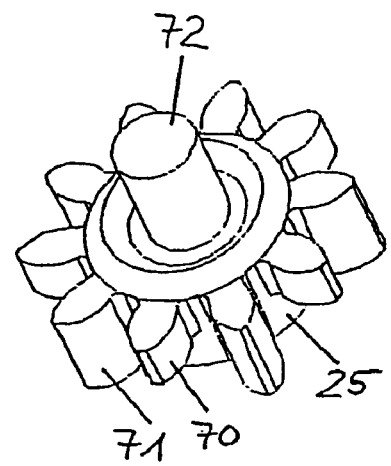
FIG. 24 shows a perspective view of an idler wheel of the dose counting unit.

FIG. 24 shows a perspective view of the idler wheel 25. The idler wheel 25 has a shaft 72 at which it is rotatably mounted on the sub-frame 20 of the dose counting sub-assembly 14 as shown in FIGS. 5A and 5B, for example. Furthermore, the idler wheel 25 has half-width teeth 70 which engage with the drive teeth 57 on the back of the units wheel 24. Furthermore, the idler wheel 25 comprises full width teeth 71 which lock against the units wheel 24. When the units wheel 24 is set to numbers "1"-"9" (reference numeral 56 in FIGS. 22A-C), the teeth 57 on the back of the units wheel 24 fit between the full-width teeth 71 of the idler wheel 25. When the units wheel 24 is set to number "0", however, the teeth 57 engage with the half-width teeth 70.

As has been explained above, the coupling between the units wheel 24 and the tens wheel 26 is such that after each ten step-wise rotations of the units wheel 24 the tens wheel 26 is rotated by one step, thereby increasing the combination of tens and hundreds numbers on the outer surface of the units wheel 24. It should be noted that FIG. 5A shows a situation in which no numbers of the units wheel 24 and the tens wheel 26 are visible through the opening 4 of the lower shell 1, since the projection 69 of the tens wheel 26 covers the respective number of the units wheel 24 so as to indicate that the medicament chamber 8 is empty.

As described above, when the flap 21 is rotated from its horizontal first position to its second position upon an inhalation process initiated by the user (see FIG. 11), the yoke 22 is slightly rotated clockwise (in FIG. 11) so that the dose protector 19 is moved from its closed position to its open position. Furthermore, by this clockwise rotation of the yoke 22, the projection or cantilever 45 of the yoke 22 is also slightly moved clockwise along the inclination of the next drive tooth 58 of the units wheel 24 so as to bring the thickening 46 of the cantilever 45 into engagement with the respective drive tooth 58. Up to this point, no actuation of the units wheel 24 and the tens wheel 26 has taken place.

After inhalation, the user closes the cover 2 of the powder inhaler. With the closing of the cover 2, the slide 15 is moved backward from its inhalation position to its filling position by means of the coupling between the projections 28 of the slide 15 and the profiled cam tracks 31 of the cover 2.

Figure 12:
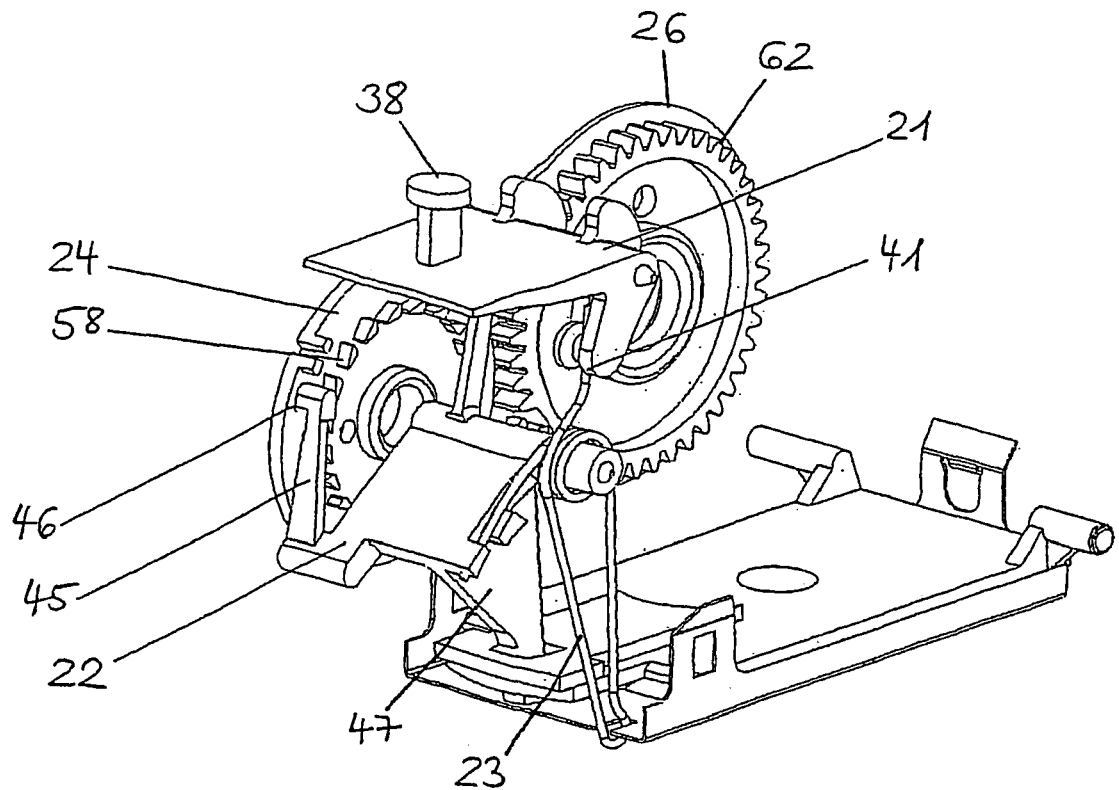
FIG. 12 shows a perspective view of the inhalation actuated mechanism and the dose counting unit of FIG. 9 after closing the cover of the powder inhaler.

As shown in FIG. 12, this backward movement of the slide 15 causes a counter clockwise rotation (as regards the view depicted in FIG. 12) of the yoke 22, since the prolongation 47 of the yoke 22 is moved together with the slide 15 backward. The counter clockwise rotation of the yoke 22 is supported by the drive spring 23 which is allowed to be discharged and decompressed upon backward movement of the slide 15. Due to this counter clockwise rotation of the yoke 22, the cantilever 45 is also rotated counter clockwise, thereby also rotating the units wheel 24 counter clockwise by one step (as regards the view depicted in FIG. 12) which results in decreasing the number of doses left in the medicament chamber 8, which is visible through the opening fear of the lower shell 1. As a matter of course, the dose counting unit can also be arranged such that it does not display the number of doses remaining in the medicament chamber 8, but the number of doses already taken by the user.

Furthermore, since the yoke 22 and the drive spring 23 are moved back into their initial positions, the end 33 of the drive spring 23 urges the flap 21 back into its horizontal first position (as shown in FIG. 12), thereby resetting the flag 38. Moreover, in this situation, the yoke 22 is again held by the engagement of its arm 43 with the feature 40 of the flap 21. Thus, the whole powder inhaler has been transferred into its initial position again.

Another advantage associated with the flag 38 is that it may be pushed down by fingers of a user so as to affect a manual override of the inhalation actuated mechanism. This would enable the user to take the dose if the user is not able to generate a sufficient force in order to actuate the inhalation actuated mechanism.

On completely closing the cover 2, there will be an audible click signaling that the cover is closed. Preferably, the powder inhaler will require the cover 2 to be completely closed to function correctly.

Finally, the deagglomerator arrangement 16 (cyclone) of the powder inhaler should be briefly discussed.

The purpose of this deagglomerator arrangement is to produce clearly defined turbulences within the inhalation channel 27 so as to pulverize agglomerations of the medicament. By the swirling airflow within the deagglomerator arrangement 16, the active part of the formulation is disaggregated from the respective carrier.

In principle the deagglomerator arrangement of the present invention comprises a rotationally symmetrical vortex chamber, at least one substantially tangential air inlet, and an outlet or exit for outputting the air with the deagglomerated powdered medicament, the outlet being spaced from the air inlet in the longitudinal axial direction of the vortex chamber. The general structure of the deagglomerator arrangement, for example, can be taken from FIG. 6A, FIG. 6B, FIG. 7A, and FIG. 17.

In addition, the structure of the deagglomerator arrangement, which is generally not restricted to the usage in powder inhalers as described in connection with the above drawings, will be explained in detail by reference to FIG. 26 and FIG. 27, respectively.

Figure 26:
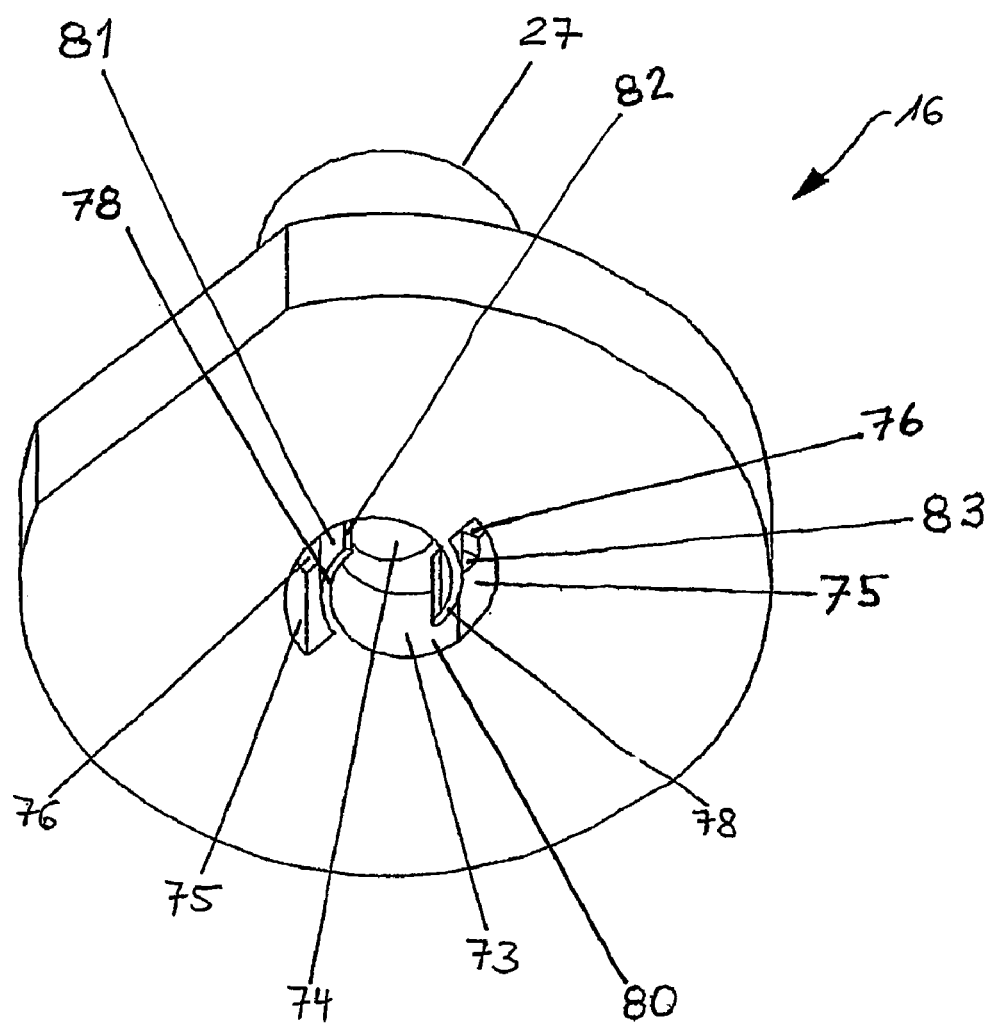
FIG. 26 shows a perspective and schematic bottom view of a deagglomerator arrangement (cyclone).

FIG. 26 shows a schematic perspective view of the deagglomerator arrangement (cyclone) according to a preferred embodiment, the deagglomerator arrangement being constructed to produce a very strong cyclonic flow within the deagglomerator arrangement resulting in a very strong velocity gradient. It is to be noted that FIG. 26 is a schematic view to explain the design and the key features of the cyclone according to the preferred embodiment, but FIG. 26 does not show the cyclone exactly as it is implemented in the above described powder inhaler. The implementation of the cyclone in the powder inhaler, for example, can be taken from FIG. 4 or FIG. 17.

As can be taken from FIGS. 26, the deagglomerator arrangement 16 has an opening in its bottom which disembogues into a vortex chamber 73. The vortex chamber 73 is designed substantially rotationally symmetrical. In addition, there are two air inlet conduits 75 which direct air substantially tangentially into the vortex chamber 73. As can be seen from FIG. 26, air inlet windows 76 are formed in the upper surface 83 of the air inlet conduits 75 which for example cover 80° of the air inlet conduits 75 so as to enable entry of air from above into the air inlet conduits 75. The base section of the vortex chamber 73, in general, has an elliptical cross-section. As depicted in FIG. 26, there is an outlet 74 formed in the upper end of the vortex chamber 73, the outlet 74 being spaced from the opening for the supply of the powdered medicament and both air inlets in the longitudinal axial direction of the vortex chamber 73. In particular, the outlet 74 is aligned coaxially to the longitudinal central axis of the vortex chamber 73 and extends along this longitudinal central axis. In particular, the outlet 74 has a substantially circular cross-section, the diameter of this circular cross-section being smaller than the diameter of the elliptical cross-section of the vortex chamber 73.

Figure 27:
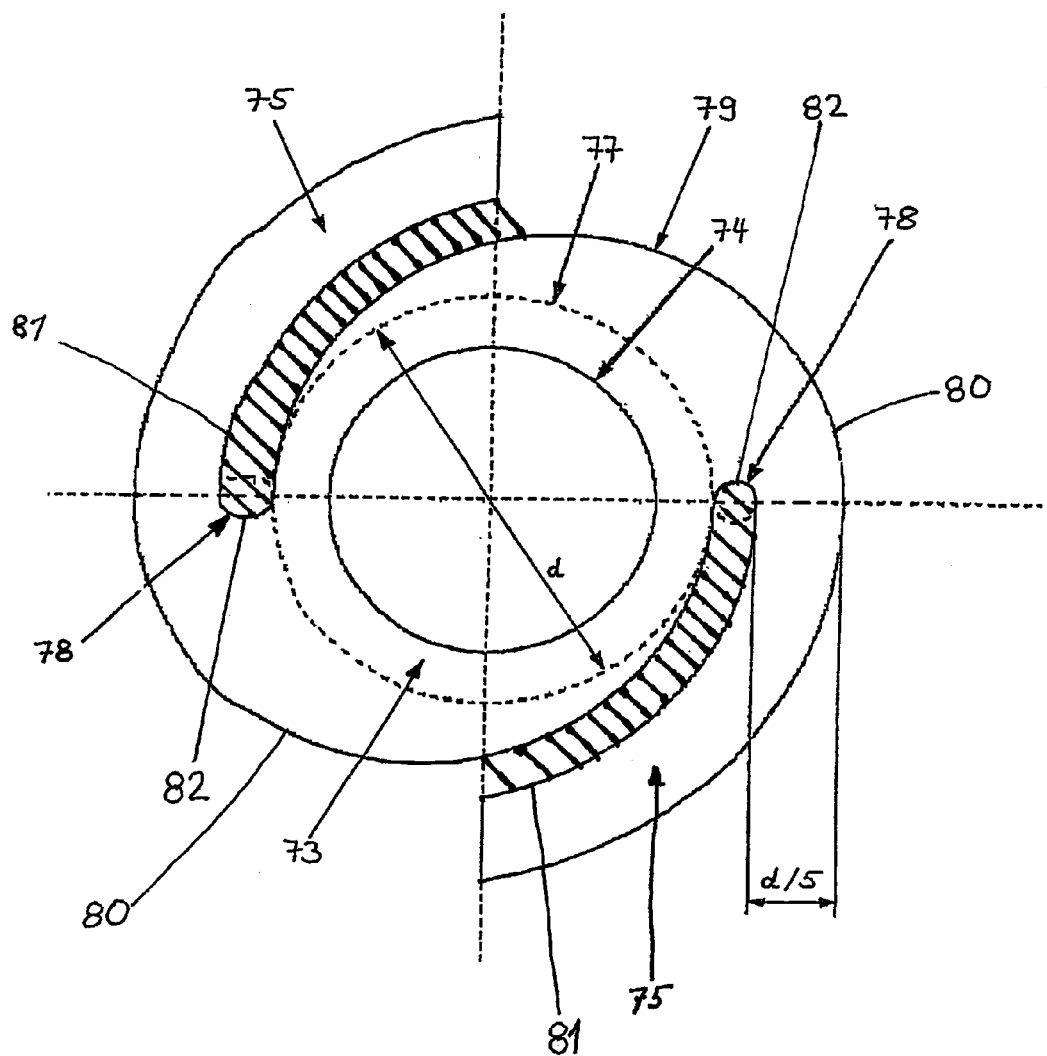
FIG. 27 shows a cross-sectional view of the deagglomerator arrangement of FIG. 26.

FIG. 27 shows a cross-sectional view of the deagglomerator arrangement in accordance with a sectional plane which horizontally intersects the deagglomerator arrangement 16 and the vortex chamber 73, respectively. The view depicted in FIG. 27 could be regarded as a bottom view of the deagglomerator arrangement 16 as well.

In FIG. 27, the vortex chamber 73 and the circular outlet 74, which disembogues into the inhalation channel 27, are depicted. Although the horizontal cross-section of the base section of the vortex chamber 73 has a substantially elliptical shape, the cross-section of the base section of the vortex chamber 73 can also be defined by an imaginary circle which can be laid inside the base section of the vortex chamber 73 on a horizontal plane intersecting both air inlet conduits 75 such that the circumference or periphery of this circle just touches the inside surfaces of both side walls 78 at places which are diametrically opposed to one another without extending beyond the side walls of the vortex chamber 73. In particular, these diametrically opposed places of the side walls 78 are those places of the side-walls 78 where both air inlets of the air inlet conduits 75 disembogue into the vortex chamber 73. In FIG. 27, the respective "base" circle is depicted with a dotted line and assigned with reference numeral 77. The air inlets are arranged along the circumference of the "base" circle 77.

Studies have shown that the diameter d of this "base" circle 77 has an important influence on the deagglomerator effect of the cyclone. For example, if the diameter d is too small, the flow resistance is too high. On the other hand, if the diameter d is too large, the flow resistance is too small resulting only in a minor improvement of the efficiency of the deagglomerator arrangement 16.

Comprehensive studies of the geometry of the deagglomerator arrangement 16 in terms of the flow resistance of the device and the quality of the cyclonic flow effected inside the vortex chamber 73 show that a very good efficiency of the device can be obtained if the diameter d is between 6 mm and 10 mm, preferably 6 mm$\leq$d$\leq$8 mm.

For example, if d is 6 mm, a flow rate of 30/min at a pressure of 4 kPa can be obtained. The cyclonic flow inside the vortex chamber 73 is of good quality. Nevertheless, the required increase in the width of the air inlets or in the outlet diameter to allow a higher target flow rate (for example 60 l/min at 4 kPa) would presumably result in a degradation of the quality of the cyclone. This is because the dimensions of the air inlets or of the outlet would be too large in comparison to the dimensions of the main section of the cyclone, which are the dimensions of the vortex chamber 73.

Therefore, it may be recommendable to use a larger diameter d of the "base" circle 77. A very compact design of the cyclone 16 and, in addition, the above-mentioned target flow rate in the range of 60 l/min at 4 kPa can be obtained if the diameter d of the "base" circle 77 is in the range of 8 mm. Larger diameters d of the "base" circle 77 do not lead to further significant improvements of the flow pattern inside the vortex chamber 73 over that which can be achieved with a diameter d=8 mm. Therefore, the diameter d=8 mm is considered as a preferred embodiment of the cyclone 16.

As depicted in FIG. 27, the deagglomerator arrangement or cyclone 16 according to this embodiment has two air inlets assigned with the respective air inlet conduits 75. Both air inlets disemboguing into the vortex chamber 73 are arranged diametrically opposed to one another and preferably have a width or a diameter of d/5. As shown in FIGS. 26 and 27, the side walls 78 separating the air inlet conduits 75 from the vortex chamber 73 end in a fillet which may have an end radius of 0.3 mm, for example. The side walls 78 may have a thickness of 0.6 mm, for example.

The cross-sectional structure of the deagglomerator arrangement 16 is such that a respective semicircle or arc 79, whose centre is on the diameter connecting both air inlets or both end portions of the side walls 78, connects the outer wall 80 of one air inlet 75 with the inner surface 81 of the opposing side wall 78 of the vortex chamber 73 at a place 82 where this side wall 78 intersects with the respective other air inlet. As can be seen from FIG. 27, this applies to both outer peripheral portions of the vortex chamber 73 and to both air inlets/air inlet conduits 75, respectively. The side walls of the air inlet conduits 75 are concentric to the side walls 78 of the vortex chamber 73. However, the semicircular or arched (curved) wall portions 79 of the vortex chamber 73 are non-concentric relative to the interior of the vortex chamber 73, i.e. the "base" circle 77. This contributes to a very effective deagglomeration within the vortex chamber 73.

The structure shown in FIG. 27 of the deagglomerator arrangement or cyclone 16 may be extruded over a height of 7.7 mm, for example. The inhalation channel 27, that is the outlet cylinder extending from the circular outlet 74, preferably has a circular diameter of 0.75 d and may be extruded on top of the vortex chamber 73 over a height of 37 mm, for example. The above-mentioned top inlet window 76, covering 80° of the air inlet conduits 75, may be extruded over 2 mm to provide the channels through which the air may enter into the device from the top of these windows.

Figure 28A:
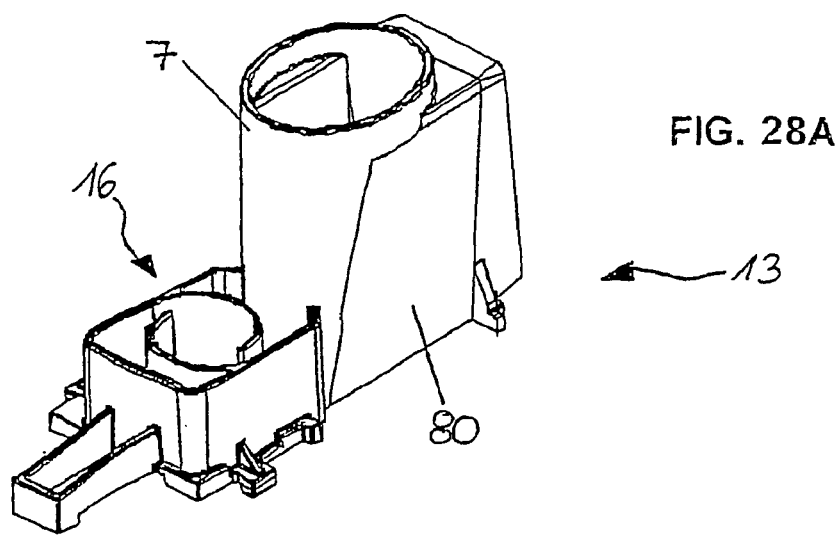
FIGS. 28A, 28B and 28C show a perspective view, a bottom view and a top view, respectively, of a dosing sub-assembly of a powder inhaler according to a further embodiment of the invention.
Figure 28B:
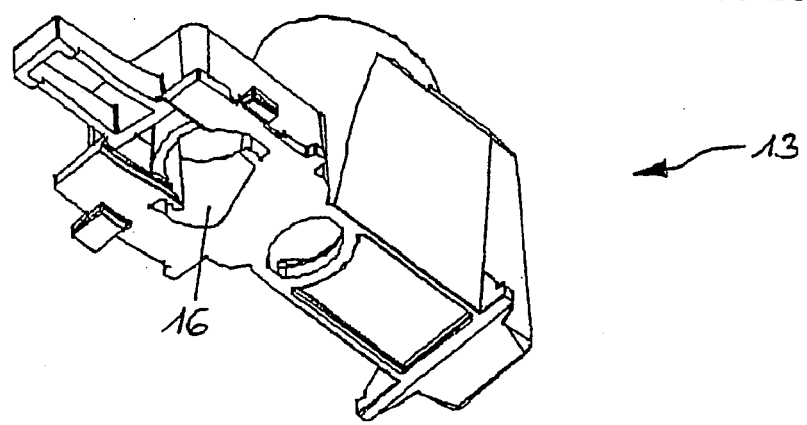
Figure 28C:
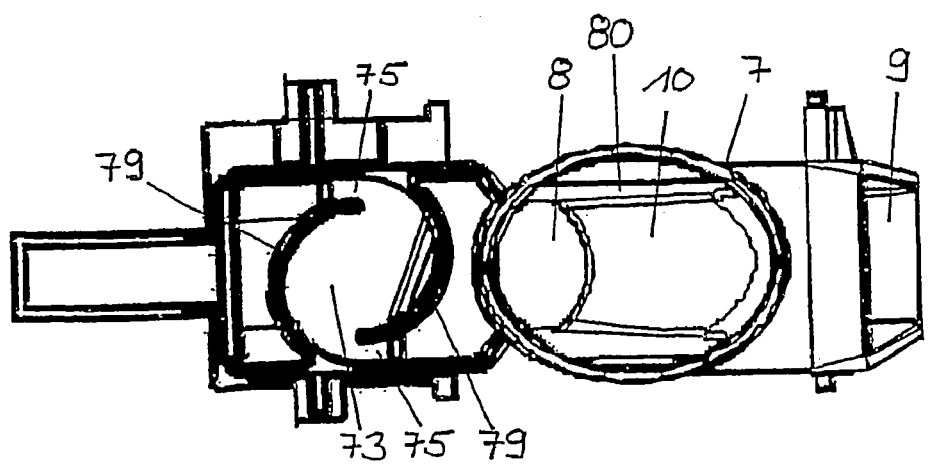

FIGS. 28A, 28B and 28C show a perspective view, a bottom view and a top view, respectively, of another embodiment of a dosing sub-assembly 13 of a powder inhaler according to the invention. As can be seen, the container 7 comprises a medicament chamber 8 having an elliptical cross-section. Inside the medicament chamber 8, side walls 80 tapering or being slanted downward are provided, thereby facilitating the filling of the dosing recess of the slide, when it is in its filling position, by gravity. Again, the desiccant chamber 9 is separated from the medicament chamber 8 by a permeable membrane 10.

The dosing sub-assembly 13 of this embodiment comprises a deagglomerator arrangement (cyclone) 16 similar to that described above. From FIG. 28C, the wall portions 79 being non-concentric to the interior diameter of the vortex chamber 73 are evident. Furthermore, FIG. 28C also shows the tangential air inlet conduits 75.

As regards the dosing sub-assembly of FIG. 28, generally reference can be made to the above description of the foregoing drawings.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A deagglomerator arrangement for deagglomerating a powdered medicament, comprising:
    a vortex chamber having an opening for supplying the powdered medicament;
    at least two air inlets for directing air tangentially into the vortex chamber, each air inlet being separated from the vortex chamber by a respective side wall; and
    an outlet for outputting air with the deagglomerated powdered medicament, the outlet being spaced from the air inlets in an axial direction of the deagglomerator arrangement,
    wherein an outer wall of each air inlet is connected to an inner surface of the respective side wall of the other air inlet by an arched wall portion of the vortex chamber, each arched wall portion being positioned non-concentric to a horizontal circle defining a diameter of the vortex chamber.

2. The deagglomerator arrangement according to claim 1, wherein the air inlets are arranged along the circle defining the diameter of the vortex chamber.

3. The deagglomerator arrangement according to claim 1, wherein the vortex chamber has a diameter d of 6 mm≦d≦10 mm.

4. The deagglomerator arrangement according to claim 3, wherein the diameter of the vortex chamber is the largest possible diameter of the horizontal circle which can be laid inside the vortex chamber on a horizontal plane intersecting the at least one air inlet without extending beyond the vortex chamber.

5. The deagglomerator arrangement according to claim 1, wherein the vortex chamber in the horizontal plane has a substantially elliptical cross-section.

6. The deagglomerator arrangement according to claim 1, wherein the vortex chamber is designed rotationally symmetrical relative to its longitudinal central axis.

7. The deagglomerator arrangement according to claim 1, wherein the vortex chamber has a diameter of about 8 mm.

8. The deagglomerator arrangement according to claim 1, wherein the at least two air inlets comprise two diametrically opposed air inlets.

9. The deagglomerator arrangement according to claim 1, wherein the at least two air inlets have a width of about d/5 with d being the diameter of the vortex chamber.

10. The deagglomerator arrangement according to claim 1, wherein the outlet is associated with a respective outlet channel having a circular cross-section.

11. The deagglomerator arrangement according to claim 10, wherein the outlet channel extends along and coaxially to the longitudinal central axis of the vortex chamber.

12. The deagglomerator arrangement according to claim 10, wherein the outlet channel has a diameter of about 0.75 d with d being the diameter of the vortex chamber.

13. The deagglomerator arrangement according to claim 1, wherein the at least two air inlets are associated with respective air inlet conduits, the vortex chamber being separated from the air inlet conduits by the side walls being concentric to the air inlet conduits.

14. The deagglomerator arrangement according to claim 13 further comprising the side walls having rounded end portions at places adjacent to the air inlets.

15. The deagglomerator arrangement according to claim 1, wherein the air inlets are associated with respective air inlet conduits, top surfaces of the air inlet conduits being exposed so as to allow entry of air into the air inlet conduits.

16. The deagglomerator arrangement according to claim 15, wherein the top surfaces of the air inlet conduits are exposed over an angle of about 80° along a circumferential direction of the air inlet conduits.

17. A powder inhaler, having:
    an inhalation channel comprising a deagglomerator arrangement for deagglomerating a powdered medicament, the deagglomerator arrangement comprising:
    a vortex chamber having an opening for supplying the powdered medicament;
    at least two air inlets for directing air tangentially into the vortex chamber with each air inlet being separated from the vortex chamber by a respective side wall; and
    an outlet for outputting air with the deagglomerated powdered medicament, the outlet being spaced from the air inlets in an axial direction of the deagglomerator arrangement,
    wherein an outer wall of each air inlet is connected to an inner surface of the respective side wall of the other air inlet by an arched wall portion of the vortex chamber, each arched wall portion being positioned non-concentric to a horizontal circle defining a diameter of the vortex chamber.

* * * * *

UNITED STATES PATENT AND TRADEMARK OFFICE
CERTIFICATE OF CORRECTION

PATENT NO.         : 7,854,226 B2
APPLICATION NO.    : 11/407520
DATED              : December 21, 2010
INVENTOR(S)        : John Pinon et al.

Page 1 of 1

It is certified that error appears in the above-identified patent and that said Letters Patent is hereby corrected as shown below:

Title page, item [75] Inventors, David Ahern should read:
Cambridge (GB); David Ahern 'Norfolk' --Welney--

Signed and Sealed this
Fourteenth Day of June, 2011

David J. Kappos
*Director of the United States Patent and Trademark Office*